US010925886B2

(12) United States Patent
Chaturvedi

(10) Patent No.: US 10,925,886 B2
(45) Date of Patent: *Feb. 23, 2021

(54) PREVENTION AND TREATMENT OF INFLAMMATORY CONDITIONS

(71) Applicant: GRI BIO, INC., La Jolla, CA (US)

(72) Inventor: Vipin Kumar Chaturvedi, Rancho Sante Fe, CA (US)

(73) Assignee: GRI BIO, INC., La Jolla, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/913,541

(22) Filed: Mar. 6, 2018

(65) Prior Publication Data

US 2018/0193368 A1 Jul. 12, 2018

Related U.S. Application Data

(63) Continuation of application No. 14/128,566, filed as application No. PCT/US2012/043875 on Jun. 22, 2012, now Pat. No. 9,949,996.

(60) Provisional application No. 61/501,139, filed on Jun. 24, 2011.

(51) Int. Cl.
*A61K 31/7032* (2006.01)
*A61K 45/06* (2006.01)
*A61K 31/07* (2006.01)
*A61K 31/203* (2006.01)
*A61K 31/192* (2006.01)
*A61K 31/4436* (2006.01)

(52) U.S. Cl.
CPC .......... *A61K 31/7032* (2013.01); *A61K 31/07* (2013.01); *A61K 31/192* (2013.01); *A61K 31/203* (2013.01); *A61K 31/4436* (2013.01); *A61K 45/06* (2013.01); *Y02A 50/30* (2018.01)

(58) Field of Classification Search
CPC .............. A61K 31/7032; A61K 31/192; A61K 31/4436; A61K 31/07; A61K 31/203; A61K 45/06; A61P 1/16
See application file for complete search history.

(56) References Cited

U.S. PATENT DOCUMENTS

| | | | |
|---|---|---|---|
| 4,837,023 A | 6/1989 | Hansjorg | |
| 5,624,957 A | 4/1997 | Swann | |
| 6,130,230 A | 10/2000 | Chambon | |
| 6,544,551 B1 | 4/2003 | Engel et al. | |
| 6,593,359 B1 | 7/2003 | Laszlo | |
| 7,419,958 B2 | 9/2008 | Wilson et al. | |
| 9,949,996 B2 | 4/2018 | Chaturvedi | |
| 2001/0018456 A1 | 8/2001 | Fesus | |
| 2003/0171251 A1 | 9/2003 | Pepys | |
| 2006/0151574 A1 | 7/2006 | Herget | |
| 2007/0087979 A1 | 4/2007 | Chaturvedi | |
| 2010/0130613 A1 | 5/2010 | Dreno | |
| 2011/0118197 A1 | 5/2011 | Chaturvedi | |
| 2015/0284320 A1 | 10/2015 | Schlechtingen et al. | |
| 2016/0067269 A1 | 3/2016 | Van Den Brink et al. | |
| 2016/0158258 A1 | 6/2016 | Chaturvedi | |

FOREIGN PATENT DOCUMENTS

| | | |
|---|---|---|
| CN | 1203528 A | 12/1998 |
| CN | 1528328 A | 9/2004 |
| EP | 0 717 995 A2 | 6/1996 |
| JP | H07-278176 | 10/1995 |
| JP | H08-333318 | 12/1996 |
| RU | 2 188 037 | 8/2002 |
| WO | WO 97/13505 | 4/1997 |
| WO | WO 2005/120479 A1 | 12/2005 |
| WO | WO 2007/071402 | 6/2007 |
| WO | WO 2007/124734 A2 | 11/2007 |
| WO | WO 2012/160186 | 11/2012 |
| WO | WO 2014/166941 A1 | 10/2014 |

OTHER PUBLICATIONS

Lee et al., Journal of Gastroenterology and Hepatology, 2012, 27 Suppl. 2, p. 75-79. (Year: 2012).*
Auke P et al, Miltefosine Supresses Inflamantion in a Mouse Model of Inflamatory Disease, Inflmaotry Bowel Diseas, vol. 19, No. 9, pp. 1974-1982, (2013).
Blomqvist et al, Multiple Tissue-Specific Isoforms of Sulfatide Activate CD1d-Restricted Type II NKT Cells, European Journal of Immunlogy, vol. 39, No. 7, pp. 1726-1735, (2009).
Bogg et al. Lysophosphatidylcholine and 1-0-0ctadecyl-2-0-Methyl-rac Glycero-3-Phosphocholine Inhibit the CDP-Choline Pathway of Phosphatidylcholine Synthesis at the CTP:Phosphocholine Cytidylyltransferase Step, Journal of Biological Chemistry, vol. 270, No. 13, pp. 7757-7764, (1995).
Dolle et al. Long Term Redution in Local Inflammation by a Lipid Raft Molecule in Atopic Dermatitis, Allergy, vol. 65, No. 9, pp. 1158-1165, (2010).
Fox et al. Recgonition of Lys-Phospholipids in Human Nautral Killer T Lymphocytes, PLOS Bilology, vol. 7, No. 10, (2009).
Hilgard, P et al., Investiagtion Into Immunological Effects of Miltefosine a New Anticancer Agent Under Development, Journal of Cancer of Research and Clinical Oncology, vol. 117, No. 5, pp. 403-408, (1991).
International Preliminary Report on Patentability dated Jun. 22, 2017 in International Application No. PCT/US2015/063930.
International Search Report and Written Opinion dated Mar. 29, 2016 in International Application No. PCT/US2015/063930.
Maricic et al., Recognition of Lysophosphatidylcholine by Type II NKT Cells and Protection from an Inflammatory Liver Disease, J. Immunol, vol. 19.., pp. 4580-4589, (2014).

(Continued)

*Primary Examiner* — Jonathan S Lau
(74) *Attorney, Agent, or Firm* — Mintz Levin Cohn Ferris Glovsky and Pepeo P.C.

(57) ABSTRACT

The present embodiments relate to methods for the prevention and treatment of inflammatory conditions such as alcoholic liver disease (ALD). More specifically the present embodiments relate to the prevention and treatment of ALD through the administration of an Retinoic Acid Receptor (RAR) agonist. Some embodiments relate to use of tazarotene in the prevention and treatment of alcohol-induced liver injury, alcohol-related liver disease, fatty liver disease, hepatic steatosis, alcoholic hepatitis or alcoholic cirrhosis.

7 Claims, 22 Drawing Sheets

(56) References Cited

OTHER PUBLICATIONS

Notification of Reexamination dated May 11, 2018 in Chinese Application No. 201280039650.6.
Notice of Allowance dated Jan. 18, 2017 in U.S. Appl. No. 14/128,566.
Notice of Allowance dated Dec. 5, 2017 in U.S. Appl. No. 14/128,566.
Office Action dated Oct. 16, 2015 in U.S. Appl. No. 14/128,566.
Office Action dated Mar. 8, 2016 in U.S. Appl. No. 14/128,566.
Office Action dated Jun. 29, 2016 in U.S. Appl. No. 14/128,566.
Office Action dated May 16, 2017 in U.S. Appl. No. 14/128,566.
Office Action dated Mar. 25, 2016 in Russian Application No. 2014100056 (with English translation).
Office Action dated Jun. 2, 2016 in U.S. Appl. No. 14/782,815.
Office Action dated Sep. 8, 2017 in Russian Application No. 2014100056 with English Translation.
Office Action dated Sep. 10, 2018 in Chinese Patent Application No. 201280039650.6 with English Translation.
Office Action dated Jul. 11, 2018 in Indian Patent Application No. 129/KOLNP/2014.
Office Action dated Jun. 21, 2018 in Canadian Patent Application No. 2,840,272.
Office Action dated Aug. 28, 2018 in Mexican Patent Application No. MX/a/2013/015441.
Office Action dated Sep. 13, 2018 in Korean Patent Application No. 2014-7001610 with English Translation.
Office Action dated Dec. 20, 2018 in U.S. Appl. No. 14/964,317.
Office Action dated Feb. 18, 2019 in European Patent Application No. 15826215.4.
Reexamination Decision dated Jan. 25, 2019 in Chinese Application No. 201280039650.6 with summary translation.
Sainii et al, Advances in Therapy for Psoriasis: An Overview of Infliximab, Etancerpt, Efalizumab Alefacept, Adalimumab, Tazarotene and Pimecrolimus, Current Pharmaceutical Design, vol. 11, pp. 273-280, (2005).
Summons to Attend Oral Proceedings Pursuant to Rule 115(1) EPC dated Nov. 12, 2018 in European Patent Application No. 12803312.3.
Weller, et al. Milefosine Innhibits Human Mast Cell Activation and Mediator Relapse Both In Vitro and Invivio, Journal of Investigative Dermatology, vol. 129, No. 2, pp. 496-498, (2009).
Zhang et al, Sulfatide-Activated Type II HKT Cells Prevent Allergic Airway Inflammation by Inhibiting Type I HK1 Cell Function in a Mouse Model of Asthma, American Journal of Physiology—Lung Cellular and Molecular Physiology, vol. 301, No. 6, pp. L974-L984, (2011).
Notice of Final Rejection dated Mar. 18, 2019 in Korean Patent Application No. 2014-7001610 with English Translation.
Declaration by Vipin Kumar Chaturvedi under 37 C.F.R. § 1.132, dated Sep. 28, 2016, filed in U.S. Appl. No. 14/128,566.
Office Action dated Feb. 26, 2019 in Canadian Patent Application No. 2,840, 272.
Office Action dated Mar. 5, 2019 in Japanese Application No. 2017-112987 with English Translation.
Office Action dated Mar. 29, 2019 in Mexican Application No. MX/a/2013/015441.
Office Action dated May 20, 2019 in Korean Patent Application No. 2014-7001610 with English Translation.
Altucci et al., RAR and RXR modulation, Nature Reviews, vol. 6, pp. 793-810, (2007).
Arrenberg et al, "Oligoclonality and innate-like features in the TCR repertoire of type II NKT cells reactive to a beta-linked self-glycolipid", Proc Natl Acad Sci U S A, 2010, vol. 107, No. 24, pp. 10984-10989.
Berni et al., "In vitro interaction of fenretinide with plasma retinol-binding protein and its functional consequences", Elsevier Science Publishers B.V., vol. 308, No. 1, pp. 43-45, Aug. 1992.
Böcher et al., "All-trans retinoic acid for treatment of chronic hepatitis C", Liver Int., Mar. 2008, vol. 28, No. 3, pp. 347-354 (also included is an abstract for the listed Böcher et al. reference, which appears to have been printed from Pubmed on the world wide web at www.ncbi.nlm.gov/pubmed/18290777 on May 19, 2016).
Bruck et al., "Additive Inhibitory Effect of Experimentally Induced Hepatic Cirrhosis by Agonists of Peroxisome Proliferator Activator Receptor γ and Retinoic Acid Receptor", Dig. Dis. Sci., vol. 54, pp. 292-299, 2009.
Busby et al., Identification of a Novel Non-Retinoid Pan Inverse Agonist of the Retinoic Acid Receptors, ACS Publications, pp. 618-627, (2017).
Bushue et al., "Retinoid pathway and cancer therapeutics", Adv Drug Deliv., vol. 62, No. 13, 2010, pp. 1285-1298.
Chandraratna, R.A.S., "Tazarotene—first of a new generation of receptor-selective retinoids", British Journal of Dermatology, vol. 135, Issue Supplement s49, pp. 18-25, Oct. 1996.
Chen, Q., "Retinoic Acid Regulates CD1d Gene Expression at the Transcriptional Level in Human and Rodent Monocytic Cells", Exp Biol Med (Maywood), Apr. 2007, vol. 232, No. 4, pp. 488-494.
Collins, S.J., "The role of retinoids and retinoic acid receptors in normal hematopoiesis", Leukemia, vol. 16, No. 10, 2002, pp. 1896-1905.
Dashtsoodol et al., "Identification of CD4 (−) CD8 (−) double-negative natural killer T cell precursors in the thymus", PLos One, vol. 3, No. 11, 2008, pp. 1-7.
Database WPI, Week 199551, Thompson Scientific, London, GB; AN 1995-400974, (1995).
Definition of Prevent, Oxford English Dictionary Online http://dictionry.oed.com/, accessed online Mar. 27, 2010, specially at defintion 9a at p. 2.
De Lalla et al., Production of Profibrotic Cytokines by Invariant NKT Cells Charcterizes Cirrhosis Progression in Chronic Viral Hepatitis, J Immunol, vol. 173, pp. 1417-1425, (2004).
Elinav, et al. Adootive Transfer of Regulatory NKT Lymphocytes Ameliorates Non-Alcoholoic Steatohepatitis and Gluclose Intolerance in ob/ob Mice and is Assoicated with Intrahepatic CD8 Trapping, J. Pathol, vol. 209, pp. 121-128, (2006).
Formelli et al., "Plasma Retinol Level Reduction by the Synthetic Retinoid Fenretinide: A One Year Follow-up Study of Breat Cancer Patients1", Cancer Research, vol. 49, pp. 6149-6152, Nov. 1, 1989.
Girardi et al., "Type II natural killer T cells use features of both innate-like and conventional T cells to recognize sulfatide self antigens", Nat Immunol, 2012, vol. 13, No. 9, pp. 851-856.
Gao B. et al, Liver natural killer and natural killer T cells: immunobiology and emerging roles in liver diseases, Journal of Leukocyte Biology, 2009, vol. 86(3), pp. 513-528.
Goranov et al. Overexpression of RARy Increases Death of SH-SY5Y Neuroblastoma Cells in Response to Retinoic Acid but not Fenretinide, Cell Death and Differentiation, vol. 13, pp. 676-679, (2006).
Grajewski et al., "Activation of invariant NKT cells ameliorates experimental ocular autoimmunity by a mechanism involving innate IFN-gamma production and dampening of the adaptive Th1 and Th17 responses", J Immunol, vol. 181, No. 7, 2008, pp. 4791-4797.
Hager C. et al, Tazarotene 0.1 % gel is associated with alterations in markers of epidermal differentiation and inflammation in psoriatic plaques, The Journal of Investigative Dermatology, 1997, vol. 108(4) pp. 656.
Halder et al., "Type II NKT cell-mediated anergy induction in type I NKT cells prevents inflammatory liver disease", J Clin Invest, 2007, vol. 117, No. 8, pp. 2302-2312.
Hammond et al. "NKT cells: Potential targets for autoimmune disease therapy?", Tissue Antigens, vol. 59, No. 5, May 1, 2002, in 11 pages.
International Search Report and Written Opinion dated Sep. 13, 2012 in International Application No. PCT/US2012/043875.
Jahng et al., "Activation of natural killer T cells potentiates or prevents experimental autoimmune encephalomyelitis", J Exp Med, 2001, Vo. 194, No. 12, pp. 1789-1799.
Jahng et al., "Prevention of autoimmunity by targeting a distinct, noninvariant CD1d-reactive T cell population reactive to sulfatide", J Exp Med, 2004, vol. 199, No. 7, pp. 947-957.
Kim et al., "The role of specific retinoid receptors in sebocyte growth and differentiation in culture", J. Invest. Dermatol., vol. 114, No. 2, pp. 349-353, Feb. 2000.

(56) References Cited

OTHER PUBLICATIONS

Kumar et al., "Different subsets of natural killer T cells may vary in their roles in health and disease", Immunology, 2014, vol. 142, pp. 321-336.
Kumar, V., "NKT-cell subsets: Promoters and protectors in inflammatory liver disease", J Hepatol, 2013, vol. 59, No. 3, pp. 618-620.
Lee et al, "Testing the NKT cell hypothesis of human IDDM pathogenesis", J Clin Invest, 2002, vol. 110, No. 6, pp. 793-800.
Maricic et al., "Dendritic Cells and Anergic Type I NKT Cells Play a Crucial Role in Sulfatide-Mediated Immune Regulation in Experimental Autoimmune Encephalomyelitis", J Immunol, 2014, vol. 193, pp. 1035-1046.
Maricic et al., "Inhibition of type I natural killer T cells by retinoids or following sulfatide-mediated activation of type II natural killer T cells attenuates alcoholic liver disease in mice", Hepatology, 2015, vol. 61, 4, pp. 1357-1369.
Maricic et al., Supplementary materials and methods to "Inhibition of type I natural killer T cells by retinoids or following sulfatide-mediated activation of type II natural killer T cells attenuates alcoholic liver disease in mice", Hepatology, 2015, vol. 61, 4, pp. 1357-6, supplementary materials in 13 pages.
Morbitzer et al., "Expression of Gastrointestinal Glutathione Peroxidase Is Inversely Correlated to the Presence of Hepatitis C Virus Subgenomic RNA in Human Liver Cells*", The Journal of Biological Chemistry, vol. 280, No. 10, pp. 8831-8841, Mar. 11, 2005.
Monto, A. et al. Steatosis in Chronic Hepatitis C: Relative Contributions of Obesity, Diabetes Melloitus and Alcohol, Heptatology, vol. 36, pp. 729-736, (2002).
Office Action dated May 11, 2015 in Chinese Patent Application No. 201280039650.6 with English Translation.
Office Action dated Feb. 2, 2016 in Chinese Patent Application No. 201280039650.6 with English Translation.
Office Action dated May 31, 2016 in Japanese Application No. 2014-517228 with English Translation.
Office Action dated Jul. 8, 2016 in Russian Application No. 2014100056.
Office Action dated Aug. 17, 2016 in Australian Application No. 2012272642.
Office Action dated Aug. 29, 2016 in Chinese Patent Application No. 201280039650.6 (with summary English translation).
Office Action dated Jan. 16, 2017 in Russian Application No. 2014100056.
Office Action dated Feb. 7, 2017 in Japanese Application No. 2014-517228.
Office Action dated Apr. 17, 2017 in Chinese Application No. 201280039650.6 with summary translation.
Office Action dated Sep. 8, 2017 in European Patent Application No. 12803312.3.
Office Action dated Dec. 18, 2017 in Mexican Application No. MX/a/2013/015441.
Office Action dated Feb. 22, 2018 in U.S. Appl. No. 14/964,317.
Office Action dated Mar. 6, 2018 in Japanese Application No. 2017-112987 with English Translation.
Office Action dated Apr. 3, 2018 in Japanese Application No. 2014-517228 with English Translation.
Pan, H. et al. Low dose ATRA Supplementation Abolishes PRM Formation in Rat Liver and Ameliorates Ethanol-induced Liver Injury, Journal of Huazhong University of Science and Technology, 2006, vol. 26(5), pp. 508-512.
Parekh et al., "Activated invariant NKT cells control central nervous system autoimmunity in a mechanism that involves myeloid-derived suppressor cells", J Immunol, 2013, vol. 190, No. 5, pp. 1948-1960.
Parekh et al., "PD-1/PD-L blockade prevents anergy induction and enhances the anti-tumor activities of glycolipid-activated invariant NKT cells", J Immunol, 2009, vol. 182, No. 5, pp. 2816-2826.
Preitner F. et al, Long-term Fenretinide treatment prevents high-fat diet-induced obesity, insulin resistance, and hepatic steatosis, American Journal of Physiology—Endocrinology and Metabolism, 2009, vol. 297, pp. E1420-E1429.
Qian et al., "Fenretinide stimulates the apoptosis of hepatic stellate cells and ameliorates hepatic fibrosis in mice", Hepatology Research, vol. 39, pp. 1229-1247, 2009.
Rao et al., "All-trans Retinoic Acid Alleviates Hepatic lschemia/Reperfusion Injury by Enhancing Manganese Superoxide Dismutase in Rats", Biol. Pharm. Bull., vol. 33, No. 5, pp. 869-875, May 2010.
Radaeva et al., "Retinoic acid signaling sensitizes hepatic stellate cells to NK cell killing via upregulation of NK cell activating ligand RAE1", Am J Physiol Gastrointest Liver Physiol, vol. 293, No. 4, 2007, pp. G809-G816.
Reyes et al., "NKT cells are necessary for maximal expression of allergic conjunctivitis", Int.Immunol, 2010; vol. 22, pp. 627-636.
Shen et al., "Invariant natural killer T cells in lupus patients promote IgG and IgG autoantibody production", Eur J Immunol, 2015, vol. 45, No. 2, pp. 612-623.
Subramanian et al., "NKT cells stimulated by long fatty acyl chain sulfatides significantly reduces the incidence of type 1 diabetes in nonobese diabetic mice", PLoS One, vol. 7, No. 5, 2012, pp. 1-11.
Supplementary European Search Report dated Nov. 13, 2014 in Application No. 12803312.3.
Supplementary European Search Report dated Jan. 26, 2015 in Application No. 12803312.3.
Syn et al. Apoptosis and Cytokines in Nonalcoholic Steatohepatitis. Clin Liver Dis. 2009, vol. 13: pp. 565-580.
The Merck Manual of Diagnosis and Therapy, 18th Edition, 2007, First Edition, 3rd Print, Section 158 pp. 1346-1347 (the cited document is in Japanese; corresponding Section 158 of the English-language version is provided as a translation).
Van Kaer, L., "Natural killer T cells as targets for immunotherapy of autoimmune diseases", Immunology and Cell Biology, vol. 82, pp. 315-322, 2004.
Verfialle, C. et al Oral R115866 in the Treatment of Moderate to Serve Facial Acene Vulgaris: An Exploratory Study, Therapeutics, (2007).
Wang et al., "Suppression of alcohol-induced hepatocellular proliferation by all-trans-retinoic acid", Alcoholism Clinical and experimental research, 24/5 Supplement, p. 188A, May 2005 (May 2005.
Yang et al., "Serum retinol binding protein 4 contributes to insulin resistance in obesity and type 2 diabetes", Nature, vol. 436, Jul. 21, 2005.
Zajonc et al., "Structural basis for CD1d presentation of a sulfatide derived from myelin and its implications for autoimmunity", Exp. Med, 2005; vol. 202, pp. 1517-1526.

* cited by examiner 5x injections, spleen proliferation

PREVENTION AND TREATMENT OF INFLAMMATORY CONDITIONS

BACKGROUND

This application is a continuation of U.S. application ser. No. 14/128,566, filed Feb. 14, 2014, which is a national stage entry, filed under 35 U.S.C. § 371, of International Application No. PCT/US2012/043875, filed Jun. 22, 2012, which claims the benefit of U.S. Provisional Application No. 61/501,139, filed Jun. 24, 2011, the entire contents of each are incorporated by reference herein in their entireties.

Field

The present embodiments relate to compositions and methods for modulating Retinoic Acid Receptor (RAR) in the prevention and treatment of inflammatory conditions of the liver.

Description of the Related Art

Excessive alcohol use is a major cause of liver disease in the Western world. Evidence of liver injury is observed in individuals who consume four or more alcoholic drinks a day (four 12 ounces beers, four glasses of wine, or four ounces of hard liquor for men or half that quantity for women). Although how alcohol damages the liver is not fully understood, chronic alcohol consumption results in the secretion of pro-inflammatory cytokines (TNF-alpha, IL6 and IL8), oxidative stress, lipid peroxidation, and acetaldehyde toxicity, resulting in inflammation, apoptosis and eventually fibrosis of liver cells.

Alcoholic liver disease (ALD) has three main phases: alcoholic fatty liver disease, alcoholic hepatitis, and cirrhosis. Alcoholic fatty liver disease, which is characterized by an accumulation of fatty acids in the liver, is usually asymptomatic and reversible if the individual abstains from alcohol for a couple of weeks. In severe cases, weakness, nausea, abdominal pain, loss of appetite, and malaise may be experienced. Although most heavy drinkers exhibit some level of fatty liver disease, in some cases, heavy drinking need only have occurred daily over a period of than less than a week, only one in five heavy drinkers develops alcoholic hepatitis, and one in four develops cirrhosis. Alcoholic hepatitis is characterized by the inflammation of hepatocytes and is generally reversible by abstinence. Cirrhosis, which is characterized by inflammation, fibrosis (cellular hardening) and damaged membranes preventing detoxification of chemicals in the body, ending in scarring and necrosis, is generally irreversible.

The cellular and molecular mechanisms underlying different phases of liver tissue damage in alcoholic liver disease are poorly understood. Although progress has been made in several areas, an effective therapeutic approach to halt this disease is still lacking. This is in part owing to the fact that the liver is a unique organ immunologically as well as anatomically. For example, while hepatic parenchymal cells have metabolic functions, non-parenchymal cells perform immunological functions. In addition to parenchymal hepatocytes, the liver contains several non-parenchymal cells such as LSEC, Kupffer cells, dendritic cells, NK cells and NKT cells that all can participate in immunity. How the immune response is orchestrated to give either tolerance or immunity to alcohol-induced damage is not known.

SUMMARY

The present embodiments generally relate to methods and compositions for modulating the innate immune system to prevent and treat tissue damage associated with inflammatory conditions. For example, several embodiments described herein relate to the prevention and treatment of alcoholic liver disease (ALD) by modulating the innate immune system.

Several embodiments described herein relate to methods and compositions for manipulating the activities of type I NKT cells and type II NKT cells, interactions between type I and type 11 NKT cells, and their interactions with other liver cells in order to treat, alleviate or prevent inflammation-associated injury to the liver. In some embodiments, the inflammation-associated injury is an alcohol-induced liver injury. In some embodiments, the alcohol-induced liver injury is alcohol-related liver disease, fatty liver disease, hepatic steatosis, alcoholic hepatitis or alcoholic cirrhosis.

Several embodiments relate to a method of preventing, mitigating or treating inflammatory induced liver damage following excessive alcohol consumption by inhibiting type I NKT cell activity. In some embodiments, pro-inflammatory type I NKT cell activity is inhibited by one or more RAR agonists selected from the group consisting of ATRA, retinol, 9-cis-RA or 13-cis-RA, tretinoin, AM580, AC55649, CD1530 and Tazarotene. In some embodiments, pro-inflammatory type I NKT cell activity is inhibited by one or more polyolefinic retinoids, such as isoretinoin and acitretin. In some embodiments, pro-inflammatory type I NKT cell activity is inhibited by one or more RAR agonists selected from the group consisting of etretinate, acitretin and isotretinoin. Several embodiments relate to the inhibition of pro-inflammatory type I NKT cell activity by tazarotene, tazarotenic acid or a mixture thereof. In some embodiments, pro-inflammatory type I NKT cell activity is inhibited by activating type 2 NKT cells. In some embodiments, inflammatory type I NKT cell activity is inhibited by one or more sulfatides.

Some embodiments of the present disclosure are related to the innate immune mechanisms leading to liver injury following, related to or caused by alcohol consumption. Some embodiments relate to manipulating the interactions among these cells which naturally provide tolerance to gut-derived or metabolite-derived antigens and at the same time provide immunity against non-self identified pathogens.

Some embodiments relate to a combination therapy approach targeting both type I and type II NKT cells for the development of an effective therapeutic to treat, prevent or mitigate tissue damage associated with inflammatory conditions. In some embodiments, an RAR agonist is used to directly inhibit type 1 NKT cell activity and a sulfatide is used to activate type II NKT cell activity.

Some embodiments relate to the prevention and treatment of tissue damage associated with ALD through the administration of all trans retinoic acid (ATRA). Several embodiments relate to use of ATRA in the prevention and treatment of alcohol-induced liver injury, alcohol-related liver disease, fatty liver disease, hepatic steatosis, alcoholic hepatitis or alcoholic cirrhosis.

Some embodiments relate to the prevention and treatment of tissue damage associated with ALD through the administration of tazarotene, tazarotenic acid or a mixture thereof. Several embodiments relate to use of tazarotene, tazarotenic acid or a mixture thereof in the prevention and treatment of alcohol-induced liver injury, alcohol-related liver disease, fatty liver disease, hepatic steatosis, alcoholic hepatitis or alcoholic cirrhosis.

Some embodiments relate to the prevention and treatment of tissue damage associated with inflammatory through the administration of one of more sulfatides. Several embodiments relate to use of sulfatide in the prevention and treatment of alcohol-induced liver injury, alcohol-related liver disease, fatty liver disease, hepatic steatosis, alcoholic hepatitis or alcoholic cirrhosis. In some embodiments, the sulfatide has following chemical structure:

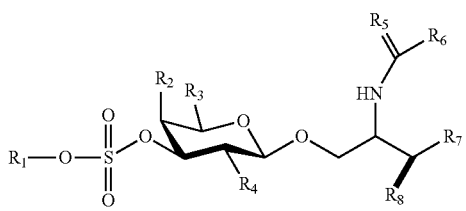

wherein $R_1$ is selected from the group consisting of a bond, a hydrogen, a $C_1$ to $C_{30}$ alkyl, $C_1$ to $C_{30}$ substituted alkyl, a $C_1$ to $C_{30}$ alkenyl, a $C_1$ to $C_{30}$ substituted alkenyl and a $C_5$ to $C_{12}$ sugar; $R_2$ is selected from the group consisting of a hydrogen, a hydroxy group, a methoxy group, and an alkoxy group; $R_3$ is selected from the group consisting of a hydrogen, a hydroxy group, a methoxy group, an ethoxy group, and an alkoxy group; $R_4$ is selected from the group consisting of a hydrogen, a hydroxy group and an alkoxy group; $R_5$ is selected from the group consisting of a hydrogen, a hydroxyl, a carbonyl, an alkoxy and a bond; $R_6$ is selected from the group consisting of a $C_1$ to $C_{40}$ alkyl, a $C_1$ to $C_{40}$ substituted alkyl, a $C_1$ to $C_{40}$ alkenyl, a $C_1$ to $C_{40}$ substituted alkenyl and a $C_1$ to $C_{40}$ alkynl; $R_7$ is selected from the group consisting of a $C_1$ to $C_{40}$ alkyl, a $C_1$ to $C_{40}$ substituted alkyl, a $C_1$ to $C_{40}$ alkenyl, a $C_1$ to $C_{40}$ substituted alkenyl and a $C_1$ to $C_{40}$ alkynl; and $R_8$ is selected from the group consisting of a hydrogen, a hydroxyl group, a carbonyl, an alkoxy group and a bond. In some embodiments, the sulfatide has following chemical structure:

ing cell proliferation in response to an in vitro challenge with αGalCer in the presence or absence of 10 ng/ml IL-2. FIG. 1c shows the results of intracytoplasmic staining of sulfatide/CD1d-tetramer+ and tetramer-populations in liver to identify IFN-γ+ cells following injection with 20 μg sulfatide. Numbers above bracket indicate % positive cells in PBS or sulfatide-injected mice. FIG. 1d shows micrographs (X200) of representative hematoxylin and eosin (H&E)-stained liver sections taken from mice at 12-96 hours following treatment with ConA alone (top row) or ConA plus bovine brain sulfatide sulfatide (bottom row). The bottom left shows a representative micrograph of an H&E-stained liver section from a control mouse injected with sulfatide alone. FIG. 1e shows graphs depicting alanine amino transferase (ALT) and aspartate amino transferase (AST) levels in IL-12p40+/+ mice at different time points after ConA (filled symbols) or ConA plus sulfatide (open symbols) injection. Vα1 ues are mean±SD of 5 mice per group. P<0.001.

FIG. 2a shows flow plots of Gr-1/CD11b expressing cells isolated from cephalad liver lobes of wild type (WT), Jα18−/− mutant and sulfatide-treated WT mice subjected to shame surgery or ischemic reperfusion injury (IRI). The boxes show the Gr-1$^{high}$ and Gr-1$^{int}$ populations analyzed in FIG. 2b. Numbers next to boxes indicate percent positive cells among liver leukocytes. FIG. 2b shows bar graphs summarizing the flow cytometric analysis. The left panel depicts the % and the right panel depicts the absolute numbers of the Gr-1$^{high}$ and Gr-1$^{int}$ populations. Vα1 ues are mean±SEM. *p<0.005. FIG. 2c shows a graph depicting the % IFN-γ+αGalCer/CD1d-tetramer+ cells in the livers of IRI, sham and sulfatide-treated IRI mice. Vα1 ues are mean±SEM. P<0.01.

FIG. 3 depicts a model for sulfatide mediation of Type I and Type II NKT cell activity. According to the model, sulfatide promotes activation of type II NKT cells, which in

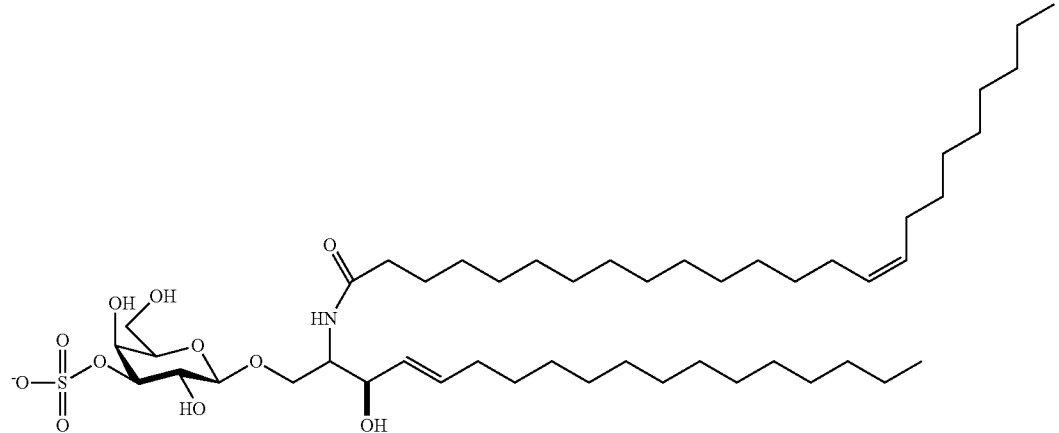

Some embodiments relate to the regulation of type I NKT cells by activated sulfatide-reactive type II NKT cells. Several embodiments relate to the regulatory role of activated sulfatide-reactive type II NKT cells on type I NKT cells in mediating protection from autoimmune disease and suppression of anti-tumor immunity.

DETAILED DESCRIPTION

Figure 1A:
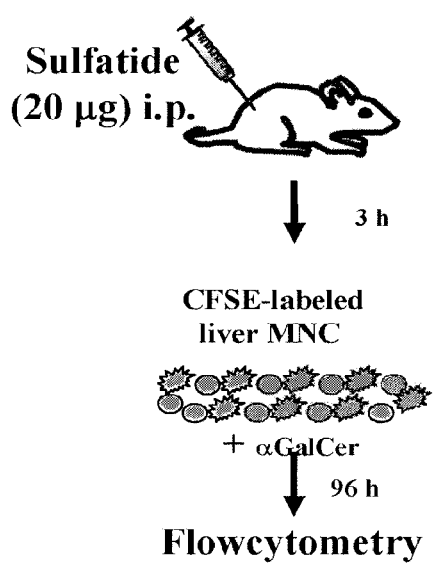
FIG. 1a depicts a methodology by which sulfatide's effect on type I NKT in the liver is determined.

The liver harbors a number of specialized cells of the innate immune system, including Kupffer cells, Natural Killer (NK) cells, Natural Killer T (NKT) cells and dendritic cells. NKT cells are unique in that they share the cell surface receptors of NK cells (e.g., NK1.1) and in addition express T cell receptors (TCR), enabling them to recognize lipid antigens in the context of CD1d molecules and bridge the innate immune responses to adaptive immunity. NKT cells have the ability to regulate the activity of other cells that contribute to inflammation of tissue and the associated cellular damage. Upon activation, NKT cells rapidly secrete large quantities IFN-γ, IL-4, granulocyte-macrophage colony-stimulating factor, as well as multiple other cytokines and chemokines. Since NKT cells are capable of secreting both Th1 and Th2 cytokines, it is difficult to predict the consequences of NKT cell activation in vivo. Depending upon context, NKT cell activation triggers cascades of events that promote or suppress different immune responses. In some contexts, activation of NKT cells leads to the activation of NK cells, dendritic cells (DCs) and B cells.

NKT cells recognize lipid antigens presented in the context of the monomorphic MHC class I-like molecule, CD1d. CD1d-restricted NKT cells are categorized into type I and type II, which recognize different lipid antigens presented by CD1d molecules. While both NKT cell subsets are predominantly NK1.1+(mouse) or CD161+/CD56+(human), their relative numbers are different in mice and humans: thus, while type I NKT cells predominate in mice, the type II NKT cell subset predominates in humans.

Type I, also known as invariant NKT cells, express a semi-invariant T cell receptor (TCR) characterized in mice by Vα14-Jα18 and Vβ8.2, Vβ7, or Vβ2 or in humans by Vα24-JαQ and Vβ11, are strongly reactive with the marine sponge-derived glycolipid α-galactosyl ceramide (αGalCer), and are identified by αGalCer/CD1d-tetramers in flow cytometry. Type I NKT cells also recognize lipid-based antigens, such as, bacterial-derived lipids and a self-glycolipid, isoglobotrihexosyl ceramide (iGb3). Type I NKT cells display memory markers and are unique in storing preformed mRNA for cytokines. Mice lacking the Jα18 gene (Jα18 mice) are deficient only in type I NKT cells.

Type II NKT cells, which are distinct from type I NKT cells, are regulatory cells that can modulate the activity of several other cell subsets, including type I NKT cells. Type II NKT cells recognize the self-glycolipid, sulfatide (3'-sulfogalactosyl ceramide) in both mice and in humans. A major subset of type II NKT cells, which can be identified using sulfatide/CD1d-tetramers in flow cytometry, predominantly utilize the Vβ8.1/Vβ3.1-Jβ2.7 and Vα1/Vα3-Jα7 gene segments and are reactive to sulfatides. Activation of type II NKT cells can be evaluated by assessing the in vitro proliferative response of type II NKT cells to a candidate agent, as well as by assessing C069 expression and cytokine secretion profile by intracellular cytokine staining or real-time PCR for IFN-γ, IL-4 or IL-13. In addition, the ability of activated type II NKT cells to anergize type I NKT cells can be evaluated by assessing the proliferative response of type I NKT cells to αGalCer (a potent activator of type I NKT cells) using CF8E-dilution analysis and intracellular cytokine staining of αGalCer/CO 1 d-tetramer cells.

Figure 2A:
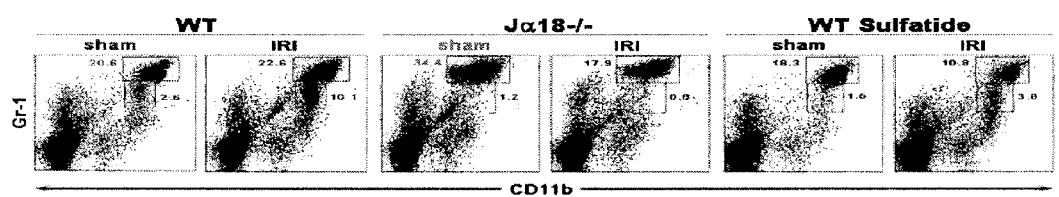

Type I and Type II NKT Cell Activity in the Liver Following of Ischemic Reperfusion Injury and Concanavalin A-Induced Hepatitis Reperfusion injury occurs when blood supply is restored to an organ or tissue after a period of ischemia. Hepatic reperfusion injury generally occurs in connection with surgery or trauma and plays a major role in the quality and function of graft tissue after liver transplant. Development of ischemic reperfusion injury (IRI) occurs in at least two phases: an initial period (following from about 1 to about 6 hours of reperfusion), which is dominated by Kupffer cell activation, release of reactive oxygen species, CD4$^+$ cell recruitment and secretion of proinflammatory cytokines, and a later period (following the initial phase from about 6 to about 48 hours of reperfusion), which is characterized by neutrophil accumulation and induction of necrosis. As shown in FIG. 2a, in wild type (WT) mice, a Myeloid (CD11b$^+$) cell subset, CD11b$^+$Gr-1$^{int}$, which comprise myeloid precursor cells and monocytes, are recruited into reperfused tissues at in the early phase of ischemia and reperfusion injury. The recruitment of myeloid cells other than neutrophils, such as the CD11b$^+$Gr-1$^{int}$ subset, suggests that injury is enhanced by recruitment of inflammatory monocytes into reperfused tissue.

Figure 4:
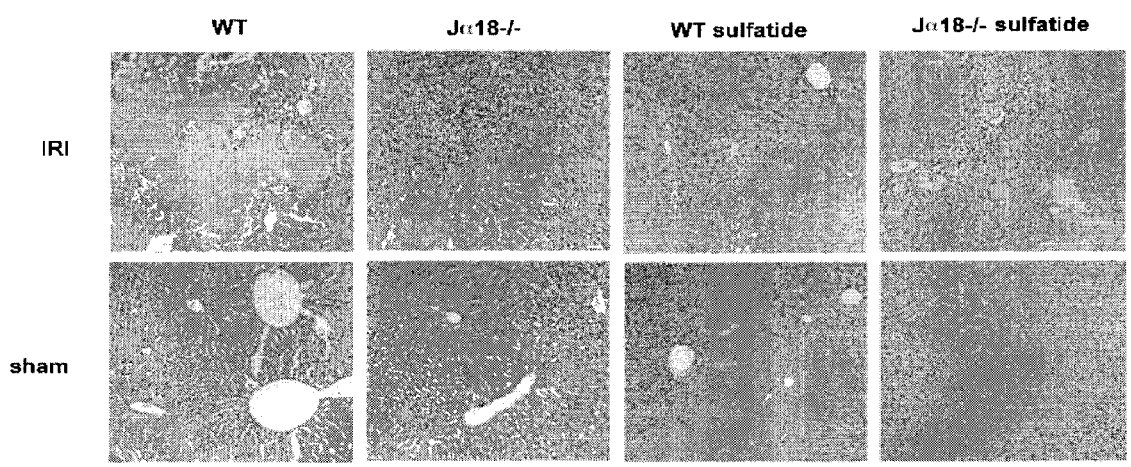
FIG. 4 show representative micrographs of H&E stained tissue from cephalad liver lobes of mice subjected to 90 min of hepatic ischemia followed by 24 hrs of reperfusion (IRI) (top row) and mice subjected to sham surgery (sham) (bottom row) at 100× magnification. From left to right, the panels show tissue from untreated WT, untreated Jα18$^{-/-}$, sulfatide-treated WT, and sulfatide-treated Jα18$^{-/-}$ mice.

Type I NKT cells also become activated and secrete IFN-γ following ischemic reperfusion. See FIG. 2c. The role of type I NKT cells in IRI was evaluated by comparing the livers of wild type (WT) and Jα18$^{-/-}$ mice, which lack type I NKT cells but have normal levels of type II NKT cells. As shown in FIG. 4, following 90 min of ischemia and 24 hrs of reperfusion, the cephalad liver lobes of WT mice had large necrotic areas whereas necrotic areas in type I NKT cell deficient mice (Jα18$^{-/-}$ mice) were remarkably reduced by comparison. This indicates a pathogenic role for type I NKT cells in mediating hepatic ischemia and reperfusion injury.

The Effect of Sulfatide-Activated NKT-2 Cells on NKT-1 Cells

As described in U.S. Pat. No. 8,044,029 and U.S. patent application Ser. No. 12/938,315, which are hereby incorporated by reference in their entirety, administration of a self-glycolipid ligand, sulfatide, as well as synthetic sulfatide analogs modulate the activity of type I and type II NKT cells. CD1d-dependent recognition of sulfatide activates type II NKT cells and predominantly plasmacytoid dendritic cells (pDC), but not conventional dendritic cell (cDC) populations (which are normally activated by type 1 NKT cells), leading to a rapid recruitment of type I NKT cells into liver in an IL-12 and MIP2-dependent fashion. However, the recruited type I NKT cells are not activated, do not secrete cytokines and become anergic.

Cellular events involved in the immunoregulatory mechanisms following sulfatide administration in vivo are shown in FIG. 1. Administration of sulfatide a) suppresses in vitro proliferation of type I NKT cells in response to stimulation by αGalCer (FIG. 1b) and b) increases the percentage of sulfatide/CD1d-tetramer+ cells with intracytoplasmic IFN-γ staining (FIG. 1c).

Secretion of IFN-γ by hepatic type I NKT cells during the early phase of ischemia and reperfusion injury is significantly decreased in mice receiving sulfatide compared to untreated animals. See FIG. 2c. Further, as with the absence of type I NKT cells in Jα18$^{-/-}$ mice, liver injury following ischemia/reperfusion is significantly reduced in mice treated with sulfatide. See FIG. 4. This indicates a pathogenic role for type I NKT cells in mediating hepatic ischemia and reperfusion injury. The role of IFN-γ secretion by type I NKT cells may be a common feature of ischemic organ injury, as kidney ischemia and reperfusion injury is also attenuated in Jα18$^{-/-}$ mice, which lack type 1 NKT.

Figure 1B:
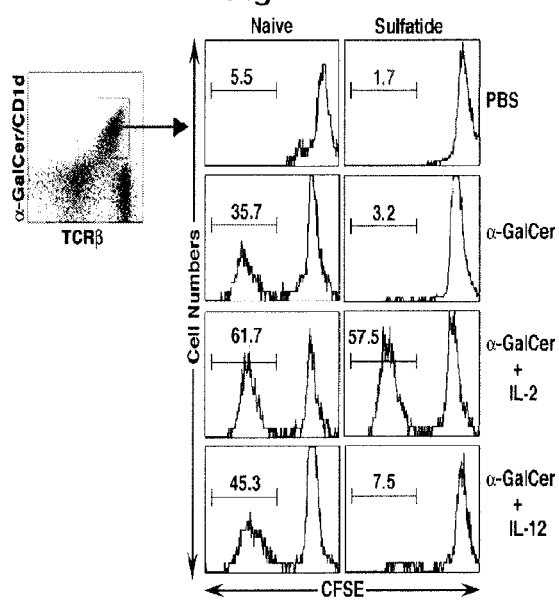
FIG. 1b shows representative data of two independent experiments measurturn inactivate type I NKT cells. Inhibition of type I NKT cells is exemplified by inhibition of IFN-γ secretion resulting in reduced hepatic recruitment of myeloid cells, granulocytes and consequently in reduced hepatocyte and endothelial cell injury.
Figure 1C:
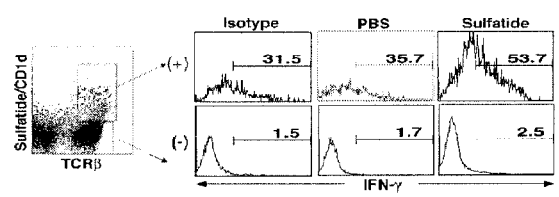
Figure 1D:
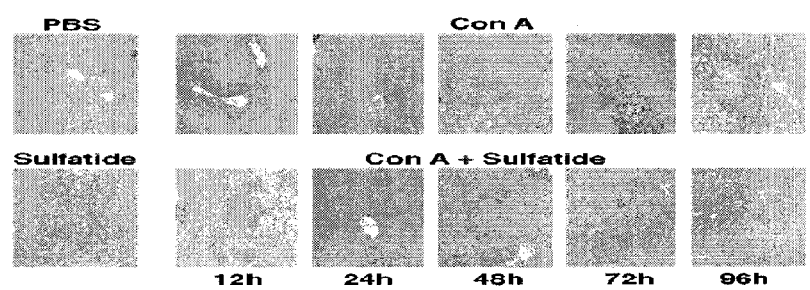
Figure 1E:
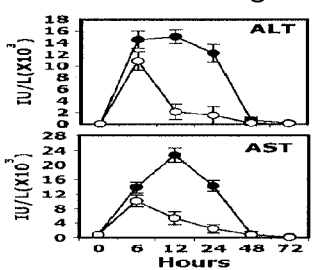

Similarly to IRI, sulfatide administration protects against Concanavalin A (ConA)-induced hepatitis as indicated by reduced hepatocellular necrosis, see FIG. 1d, and reduced serum levels of alanine aminotransferase (ALT) and aspartate amino transferase (AST), markers of hepatocellular damage, see FIG. 1e. This indicates a pathogenic role for type I NKT cells in ConA-induced hepatitis.

Figure 3:
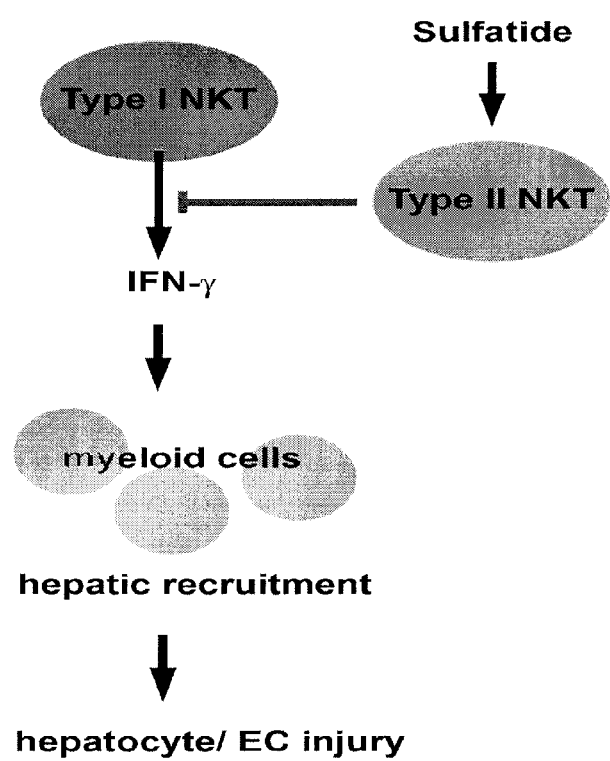

Collectively, data from both models of liver damage, IRI and ConA-induced hepatitis, are consistent with an immunoregulatory pathway in which type I NKT cells play a detrimental role and sulfatide-reactive type II NKT cells play a protective role in hepatic inflammation arising from diverse causes. Such protection is associated with the inhibition of cytokine secretion by type I NKT cells (inhibited phenotype) and a significant reduction in hepatic recruitment of immature myeloid cells (CD11b+Gr-1+) CD11b+Gr-1– and NK cells. Inhibition in type I NKT cells is also associated with the tolerization or modification of conventional dendritic cells (cDCs) and they together with inhibited type I NKT cells inhibit activation/expansion of adaptive Th1/Th17 CD4+/CD8+ T cells. This leads to a model where administration of sulfatide stimulates the activity of type II NKT cells, which in turn inhibit type I NKT cell activity and the liver damage caused by type I NKT cell-mediated inflammation. See FIG. 3.

Role of NKT Cells in Alcoholic Liver Disease

Figure 5:
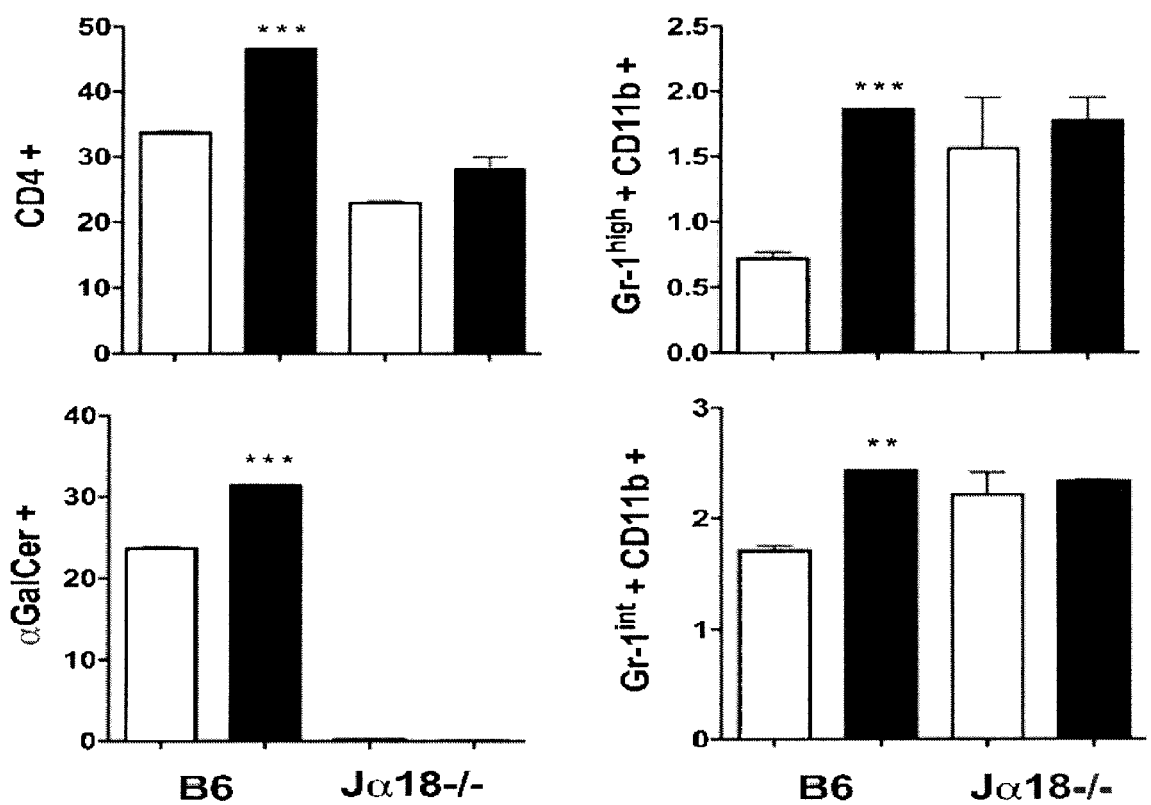
FIG. 5 shows graphs summarizing flow cytometry analysis of liver MNCs isolated from groups (4 in each) of male BL/6 WT or Jα18-/- mice following 5 weeks of feeding with a liquid Lieber-Decarli diet containing 5% ethanol or control diet containing similar number of calories. P values <0.005. Accumulation of activated type I NKT cells and CD11b+Gr-1+ myeloid cells was observed in the livers of WT but not Jα18-/- mice.

Alcoholic Liver Disease (ALD) develops as a result of damage to liver cells caused by excess alcohol consumption. Multiple insults may be required before clinical manifestations of ALD are observed. However, as described herein, significantly increased numbers of type I NKT cells (αGalCer/CD1d-tetramer+ cells), CD4+ cells, and CD11b+ Gr-1+ myeloid cells, but not type II NKT cells or CD11b+ Gr-1− cells, are observed in the liver following chronic alcohol consumption. See Example 6 and FIG. 5. Enhanced expression of CD69 marker further indicates that type 1 NKT cells are partially activated. Thus, even in the absence of any clinical signs of disease (preclinical phase) cells mediating an inflammatory response accumulate in the liver following excess alcohol consumption. In the absence of type I NKT cells (Jα18−/− mice), accumulation of CD11b+ Gr-1+ myeloid cells in the liver following chronic alcohol consumption is significantly reduced. See Example 6 and FIG. 5. These data suggest that type I NKT cells are involved in mediating the preclinical phase of ALD.

Consistent with the data suggesting a role for type I NKT cells in the preclinical phase of ALD, clinical manifestations of liver damage following excessive alcohol consumption are significantly reduced, as measured, for example, by histology and liver enzyme analysis, in type I NKT cell deficient (Jα18−/−) mice. See Example 6 and FIGS. 6 and 7. These data suggest that type I NKT cells play an important role in alcoholic damage to the liver.

NKT cells express T cell receptors, which enable them to recognize lipid antigens in the context of CD1d molecules. Not wishing to be bound by a particular theory, type I NKT cells are activated in the liver following ethanol consumption by local presentation of oxidized self-lipids by CD1d-expressing antigen presenting cells (APCs). Activated type I NKT cells then initiate a multistep process resulting in Kupffer cell activation, recruitment/activation of granulocytes followed by inflammatory damage to hepatocytes.

The interplay among NKT cell subtypes following alcohol consumption sets the stage for liver damage and in severe cases, alcoholic liver disease (ALD). Several embodiments described herein relate to methods and compositions for manipulating the opposing roles of type I NKT cells and type II NKT cells and their interactions with other liver cells in order to treat, alleviate or prevent injury to the liver following alcohol consumption.

Several embodiments described herein relate to modulating the activity of NKT cell subtypes in order to treat, mitigate or prevent alcohol-induced injury to the liver. As described herein, administration of sulfatide or retinoic acid receptor (RAR) agonists inhibits alcohol-induced liver damage. For example, injections of sulfatide or retinoic acid receptor (RAR) agonist, All-trans Retinoic Acid (ATRA), during chronic alcohol consumption and prior to ethanol binge had a protective effect as shown by histological examination and analysis of liver enzyme levels in serum. See Example 7 and FIGS. 6 and 7.

Several embodiments relate to a protective role in alcohol induced liver injury for a major subset of type II NKT cells, which are reactive to sulfatide. Activation of this NKT cell subset by sulfatide inhibits type I NKT cell-mediated injury following excess alcohol consumption. Sulfatide-mediated protection is associated with activation of type II NKT cells and inhibition of IFN-γ secretion by hepatic type I NKT cells and suppression of type I NKT cell-mediated recruitment of myeloid cells, for example, the CD11b$^+$Gr-1$^{int}$ and Gr-1− subsets, and NK cells into the liver.

Sulfatide treatment results in almost complete protection from liver damage following excess alcohol consumption. See FIGS. 6 and 7. Not wishing to be bound by a particular theory, the protective effect of sulfatide is mediated through the direct activation of Type II NKT cells, which exert an inhibitory effect on type I NKT cells and cDCs.

T cell lines from peripheral blood lymphocytes (PBL) of two healthy donors were generated following in vitro stimulation with either αGalCer or sulfatide and analyzed by flow cytometry. Around 2% of the T cells stain with sulfatide/hCD1d-tetramers in this cell line following two cycles of stimulation. Similar to the murine system, these cells do not use the invariant Vα24-Vα11 TCR. These data show the presence of sulfatide-reactive type II NKT cells in healthy individuals and indicate the effectiveness of using sulfatide/humanCD1d-tetramers in the characterization of human type II NKT cells in alcoholic liver disease.

In some embodiments, the sulfatide can be, for example, bovine brain-derived sulfatide, which is a mixture of about 20 different species obtained from Sigma Inc. (Chicago, Ill., USA). In other embodiments, the sulfatide is semisynthetic and is a single species of sulfatide, for example, cis-tetracosenoyl sulfatide or lysosulfatide obtained from Maitreya Inc, (Pleasant Gap, Pa., USA). In still other embodiments, the sulfatide can be a totally synthetic sulfatide.

Sulfatide derived from bovine brain myelin is comprised of a 2:1 mixture of saturated/unsaturated major acyl chains ($C_{24}$), with unsaturation occurring at $C_{19}$. Several embodiments relate to the use of synthetic sulfatide analogs, such as analogs with saturated acyl chain ($C_{24}$) and unsaturated chains ($C_{24}$: 1) as well as analogs comprised of different lengths of acyl chains in the fatty acid or sphingosine moiety (shorter as well as longer, for example, $C_{18}$, $C_{32}$) and positional isomers with 3' vs. 4'-sulfated group on the galactose moiety (3'-803 vs. 4'-803).

In some embodiments the sulfatide has the following chemical formula I:

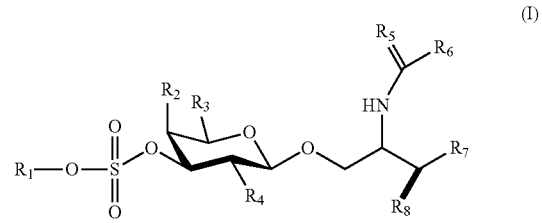

wherein $R_1$ can be a bond, a hydrogen, a $C_1$ to $C_{30}$ alkyl, a $C_1$ to $C_{30}$ substituted alkyl, a $C_1$ to $C_{30}$ alkenyl, a $C_1$ to $C_{30}$ substituted alkenyl or a $C_5$ to $C_{12}$ sugar; $R_2$ can be a hydrogen, a hydroxy group, a methoxy group, or an alkoxy group; $R_3$ can be a hydrogen, a hydroxy group, a methoxy group, an ethoxy group, or an alkoxy group; $R_4$ can be a hydrogen, a hydroxy group or an alkoxy group; $R_5$ can be a hydrogen, a hydroxy group, a carbonyl, an alkoxy group or a bond; $R_6$ can be a $C_1$ to $C_{40}$ alkyl, a $C_1$ to $C_{40}$ substituted alkyl, a $C_1$ to $C_{40}$ alkenyl, a $C_1$ to $C_{40}$ substituted alkenyl, or a $C_1$ to $C_{40}$ alkynl; $R_7$ can be a $C_1$ to $C_{40}$ alkyl, a $C_1$ to $C_{40}$ substituted alkyl, a $C_1$ to $C_{40}$ alkenyl, a $C_1$ to $C_{40}$ substituted alkenyl, or a $C_1$ to $C_{40}$ alkynl; and $R_8$ can be a hydrogen, a hydroxy group, a carbonyl, an alkoxy group or a bond.

In other embodiments, the sulfatide has the following chemical formula II:

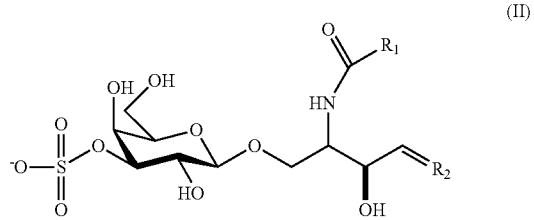

(II)

wherein $R_1$ is selected from the group consisting of a $C_1$ to $C_{40}$ alkyl, a $C_1$ to $C_{40}$ substituted alkyl, a $C_1$ to $C_{40}$ alkenyl, a $C_1$ to $C_{40}$ substituted alkenyl and a $C_1$ to $C_{40}$ alkynl; and $R_2$ is selected from the group consisting of a hydrogen, a hydroxyl group, a carbonyl, an alkoxy group and a bond.

In another embodiment, the sulfatide has the following chemical structure:

stituted alkyl." Cyclic compounds, both unsaturated cyclic hydrocarbons and cyclic compounds having heteroatoms, are within the meaning of "alkenyl."

As used herein, the term "alkoxy" refers to any unbranched, or branched, substituted or unsubstituted, saturated or unsaturated ether.

As used herein, the term "sulfatide" retains its general accustomed meaning and refers to a cerebroside sulfuric ester containing one or more sulfate groups in the sugar portion of the molecule.

As used herein, the term "cerebroside" refers to any lipid compound containing a sugar, and generally of the type normally found in the brain and nerve tissue.

The compounds of formula (I), (II) and (III) may be in the form of pharmaceutically acceptable nontoxic salts thereof. Salts of formula (I), (II) and (III) include acid added salts, such as salts with inorganic acids (e.g., hydrochloric acid, sulfuric acid, nitric acid and phosphoric acid) or with organic acids (e.g., acetic acid, propionic acid, maleic acid,

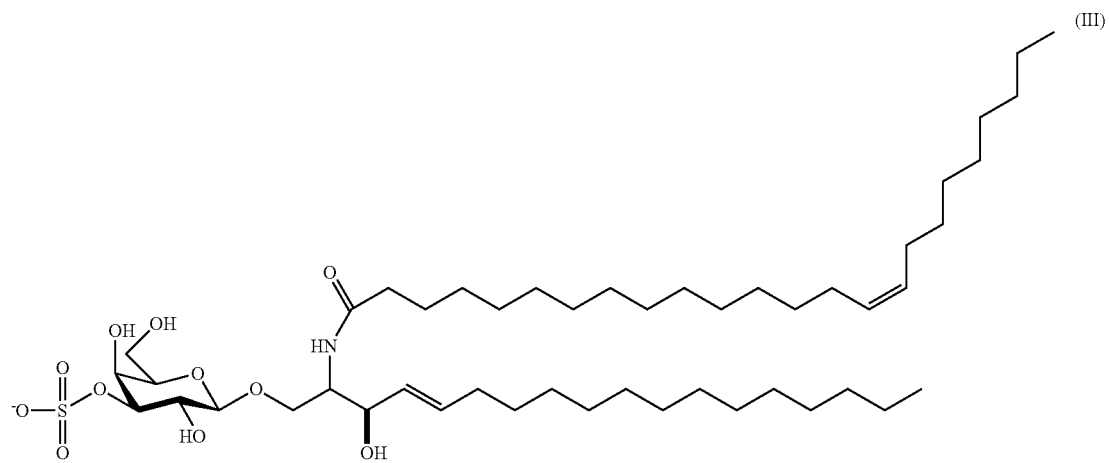

(III)

As used herein, the term "alkyl" means any unbranched or branched, saturated hydrocarbon. The term "substituted alkyl" means any unbranched or branched, substituted saturated hydrocarbon. Cyclic compounds, both cyclic hydrocarbons and cyclic compounds having heteroatoms, are within the meaning of "alkyl."

As used herein, the term "substituted" means any substitution of a hydrogen atom with a functional group.

As used herein, the term "functional group" has its common definition, and refers to chemical moieties preferably selected from the group consisting of a halogen atom, $C_1$-$C_{20}$ alkyl, substituted $C_1$-$C_{20}$ alkyl, perhalogenated alkyl, cyloalkyl, substituted cycloalkyl, aryl, substituted aryl, benzyl, heteroaryl, substituted heteroaryl, cyano, and nitro.

As used herein, the terms "halogen" and "halogen atom" refer to any one of the radio-stable atoms of column 17 of the Periodic Table of the Elements, preferably fluorine, chlorine, bromine, or iodine, with fluorine and chlorine being particularly preferred.

As used herein, the term "alkenyl" means any unbranched or branched, substituted or unsubstituted, unsaturated hydrocarbon. The term "substituted alkenyl" means any unbranched or branched, substituted unsaturated hydrocarbon, substituted with one or more functional groups, with unbranched $C_2$-$C_6$ alkenyl secondary amines, substituted $C_2$-$C_6$ secondary alkenyl amines, and unbranched $C_2$-$C_6$ alkenyl tertiary amines being within the definition of "suboleic acid, palmitic acid, citric acid, succinic acid, tartaric acid, fumaric acid, glutamic acid, pantothenic acid, laurylsulfonic acid, methanesulfonic acid and phthalic acid).

The compounds of formula (I), (II) and (III) may be in the form of solvates thereof (e.g., hydrates).

The compounds of formula (I), (II) and (III) can be produced by any purposive method to synthesize sulfatides.

The compounds of formulas (I), (II) and (III) can also be isolated from natural products (e.g., biological organisms) and purified by column chromatography or the like.

In one embodiment, the sulfatide has the chemical formula: (2S, 3R, 4E)-N-nervonic-1-[-D-(3-sulfate)-galactopyranosyl]-2-amino-octadecene-3-ol. This chemical formula is also referred to as cis-tetracosenoyl sulfatide.

In some embodiments, the specific amount of sulfatide administered to a patient will vary depending upon the disease or condition being treated, as well as the age, weight and sex of the patient being treated. Generally, to achieve such a final concentration in, e.g., the intestines or blood, the amount of sulfatide molecule in a single dosage composition of the present embodiments will generally be about 0.1 milligrams to about 100 milligrams, preferably about 2.0 milligrams to about 60 milligrams, more preferably about 20 milligrams to about 50 milligrams. Likewise, the amount of a secondary therapeutic compound in a single oral dosage composition of the present embodiments will generally be in the range of about 0.01 milligrams to about 1000 milligrams, more preferably about 0.1 milligrams to about 100 milligrams. Obviously, the exact dosage will vary with the disease or disorder being treated, the preferred ranges being readily determinable.

In one embodiment, 0.1-10 mg/kg body weight of sulfatide are administered to the patient. More preferably, 1-10 mg/kg body weight of sulfatide are administered. Preferably, this dosage is repeated each day as needed.

Effect of Retinoic Acid Receptor (RAR) Agonists on NKT Cell Activity

Figure 10:
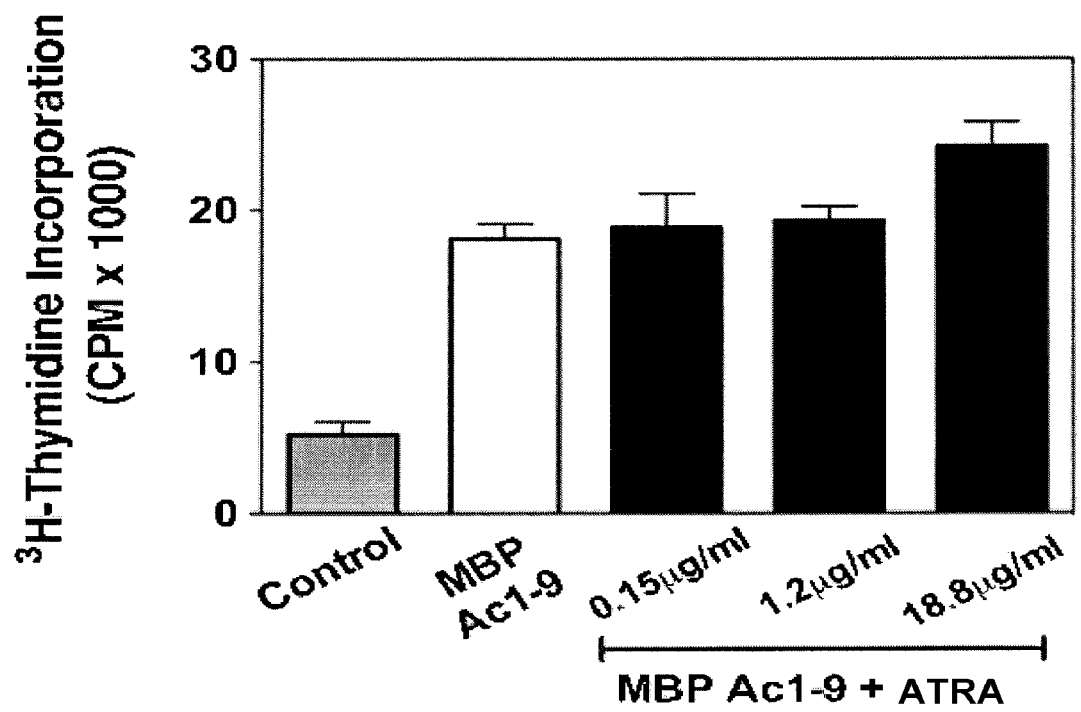
FIG. 10 shows a bar graph depicting proliferation (as measured by [$^3$H]-thymidine incorporation) of freshly isolated myelin basic protein MBPAc1-9-reactive CD4+ T cells isolated from naïve B10.PL Vβ8.2 TCR transgenic mice in response to stimulation with MBPAc1-9 alone or MBPAc1-9 and graded concentrations of ATRA (0.15, 1.2, 18.8 μg/ml).

As described herein, administration of the Retinoic Acid Receptor (RAR) agonist, all trans retinoic acid (ATRA), significantly inhibits liver damage caused by alcohol consumption. Ethanol ingestion depletes liver retinyl esters and alters physiological levels of all trans retinoic acid (ATRA), a biologically active from of vitamin A that supports many biological functions and can enhance generation, stability and function of naïve CD4+ T cell differentiation into FoxP3+ Tregs even in the presence of IL-6. Several embodiments described herein relate to the finding that ATRA inhibits type I NKT cell effector function, including suppressing cytokine secretion by these cells. See Examples 8, 9 and 11 and FIGS. 8, 10, and 11. Further, ATRA has a direct inhibitory effect on type I NKT cell activity, exerting its inhibitory effect in the absence of antigen-presenting cells. See Example 11, FIG. 11. In addition, ATRA does not directly inhibit the activity of conventional MHC-restricted CD4+ T cells that recognize protein antigens, such as myelic basic protein or MBPAc1-9. Not wishing to be bound by a particular theory, these data indicate that ATRA protects against liver damage caused by excessive alcohol consumption by inhibiting type I NKT cells.

As described herein, RAR agonists induce inhibition in type I NKT cells. See FIGS. 12, 14 and 15-17. Further, liver damage caused by type I NKT cell mediated inflammation resulting from excess alcohol consumption can be prevented, reduced or mitigated by administration of an RAR agonist. The liver can become inflamed for a variety of different reasons. For example, liver inflammation can be caused by bacterial or viral infection, injury, or attack from one's own immune system. While inflammation is normally a protective response and a required step of the healing process, prolonged or chronic inflammation can cause injury. Several embodiments described herein relate to the RAR agonist mediated modulation of the innate immune mechanisms leading to liver injury following, related to or caused by inflammation. Some embodiments relate to methods and compositions for RAR agonist mediated inhibition of type I NKT cell activity which modulate interactions among the components of the innate immune system to provide tolerance to gut-derived or metabolite-derived antigens without affecting or minimally affecting the innate immune response to non-self identified pathogens.

As RAR agonists can directly anergize Type I NKT cells, RAR agonists may be used to treat any indication in which Type I NKT cells play a pathogenic role. Some examples of diseases which can be treated by the embodiments of the present disclosure include, alcohol induced hepatitis, non-alcoholic steatosis hepatitis, cirrhosis, fulminating cirrhosis, idiopathic hepatitis, viral-induced hepatitis (A, B, C and other), inflammatory hepatitis associated with hepato-biliary carcinoma, multiple sclerosis, type 1 diabetes, ischemic reperfusion injury, solid organ transplantation, systemic lupus erythematosus, rheumatoid arthritis, amyotrophic lateral sclerosis, and inflammatory bowel disease (Crohn's and colitis).

In some embodiments, are various indications of autoimmune or immune related diseases or disorders are treated, prevented or mitigated by RAR agonist mediated inhibition of type I NKT cell activity. In particular, one aspect of the present embodiment is related to a method of treating a patient suffering from symptoms of an autoimmune or immune related disease or disorder, such as, for example, multiple sclerosis, systemic lupus erythematosus, AIDS, Alzheimer's disease, rheumatoid arthritis, insulin dependent diabetes mellitus, autoimmune hepatitis, asthma, and celiac disease with an effective amount of an RAR agonist. In some embodiments, RAR agonist mediated inhibition of type I NKT cell activity treats, prevents or mitigates asthma symptoms.

Some embodiments relate a method of inhibiting or preventing type I NKT cell mediated inflammation following ischemic reperfusion by administering an RAR agonist. Type I NKT cells play a pathogenic role in conditions such as ischemia and reperfusion injury. Reperfusion injury can occur in a variety of tissues when blood supply is restored after a period of ischemia. Examples include skeletal muscle tissue following a crush injury, cardiac muscle in connection with a myocardial infarction or cardiac surgery, or ischemic heart disease, neural tissue in connection with a stroke or brain trauma, and hepatic and renal tissue in connection with surgery or trauma. Ischemic reperfusion injury also plays a major role in the quality and function of graft tissue in organ transplant. Ischemia and reperfusion injury is a major cause for increased length of hospitalization and decreased long-term graft survival. In some embodiments, RAR agonist mediated inhibition of type I NKT cell activity inhibits or prevents hepatic ischemic reperfusion injury in connection with surgery or trauma.

Embodiments described herein relate to the inhibition of type I NKT cell activity by one or more retinoic acid receptor (RAR) agonists. Retinoic acid receptors comprise three major subtypes: RARα, RAR β, and RARγ. Some embodiments relate to the inhibition of type I NKT cell activity by one or more pan-active RAR agonists, precursors of such pan-active RAR agonists and mixtures thereof. As used herein, the term "pan-active RAR agonist" refers to a RAR agonist which affects, for example, activates, RARα, RARβ, and RARγ substantially equally or non-selectively. Some embodiments relate to the inhibition of type I NKT cell activity by one or more active RAR agonists effective to selectively, or even specifically, affect, for example, activate, at least one, and preferably both, of RARβ and RARγ relative to RARα, precursors of such active RAR agonists and mixtures thereof. As used in this context, the term "selectively" means that the RAR agonist precursors of the RAR agonist and mixtures thereof are more effective, preferably at least about 10 or about 100 times to about 1000 times or more as effective, to affect at least one, and preferably both, of RAR β and RARγ relative to RARα. Some embodiments relate to the inhibition of type I NKT cell activity by one or more subtype-selective RAR agonists, precursors of such subtype-selective RAR agonists and mixtures thereof. As used herein, the term "subtype-selective RAR agonist" refers to a RAR agonist which selectively affects, for example, activates one RAR subtype. Retinoid compounds having RARα, RAR β, and RARγ-selectivity are known in the art and disclosed, for example, in U.S. Pat. Nos. 6,534,544 and 6,025,388 which are herein incorporated by reference in their entirety.

Several embodiments relate to a method of inhibiting pro-inflammatory type I NKT cell activity by administering one or more retinoic acid receptor (RAR) agonists. Examples of RAR agonists include, but are not limited to, the RAR agonists listed in Table 1.

TABLE 1

| Compound Name | Specificity | Structure |
| --- | --- | --- |
| Tretinoin | Pan-RAR agonist | 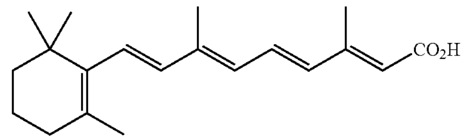 [SMILES: CC1=C(/C=C/C(C)=C/C=C/C(C)=C/C(=O)O)C(C)(C)CCC1] |
| 9-cis RA | Pan-RAR and RXR agonist | 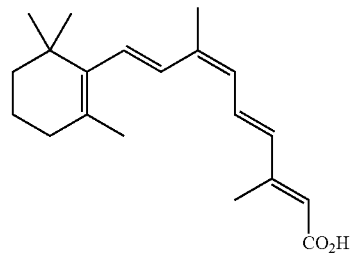 [SMILES: CC1=C(/C=C/C(C)=C\C=C\C(C)=C\C(=O)O)C(C)(C)CCC1] |
| 13-cis-RA | Pan-RAR agonist | 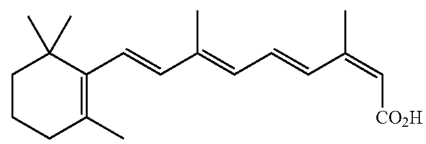 [SMILES: CC1=C(/C=C/C(C)=C/C=C/C(C)=C\C(=O)O)C(C)(C)CCC1] |
| Fenretinide | RAR agonist<br>RAR-independent effects | 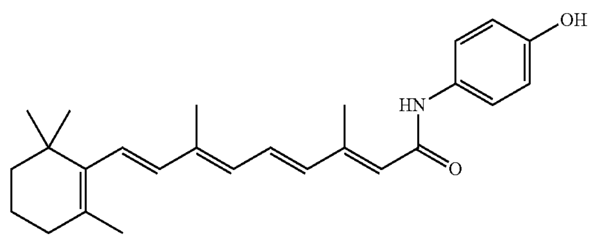 [SMILES: CC1=C(/C=C/C(C)=C/C=C/C(C)=C/C(=O)Nc2ccc(O)cc2)C(C)(C)CCC1] |
| EC 23 | Pan-RAR agonist | 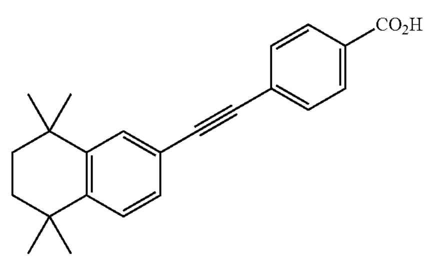 [SMILES: CC1(C)CCC(C)(C)c2cc(C#Cc3ccc(C(=O)O)cc3)ccc21] |
| TTNPB | Pan-RAR agonist | 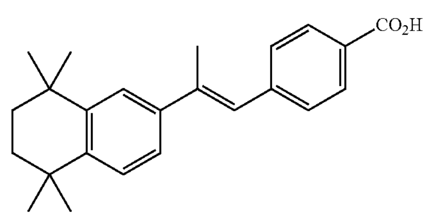 [SMILES: C/C(=C\c1ccc(C(=O)O)cc1)c1ccc2c(c1)C(C)(C)CCC2(C)C] |
| Ch 55 | Pan-RAR agonist | 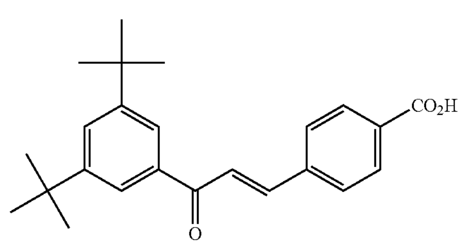 [SMILES: CC(C)(C)c1cc(C(=O)/C=C/c2ccc(C(=O)O)cc2)cc(C(C)(C)C)c1] |

TABLE 1-continued

| RAR agonists | | |
|---|---|---|
| Compound Name | Specificity | Structure |
| Tazarotene | RARβ/γ agonist | |
| BMS 753 | RARα agonist | |
| AM80 | RARα agonist | |
| AM580 | RARα agonist | |
| AC55649 | RARβ2 agonist | |
| AC261066 | RARβ2 agonist | |
| Adapalene | RARβ and γ agonist | |

TABLE 1-continued
RAR agonists
| Compound Name | Specificity | Structure |
| --- | --- | --- |
| CD437 | RARγ agonist | 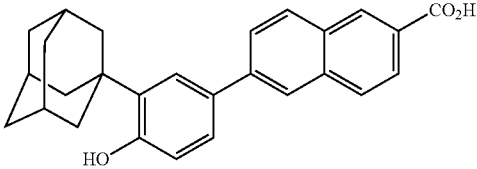 [SMILES: O=C(O)c1ccc2cc(-c3ccc(O)c(C45CC6CC(CC(C6)C4)C5)c3)ccc2c1] |
| CD1530 | RARγ agonist | 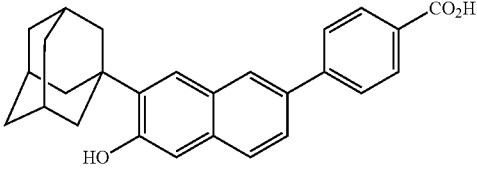 [SMILES: O=C(O)c1ccc(-c2ccc3cc(O)c(C45CC6CC(CC(C6)C4)C5)cc3c2)cc1] |
| CD2665 | RARγ agonist | 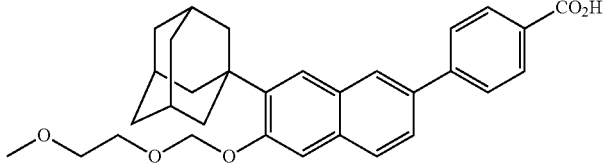 [SMILES: COCCOCOc1cc2ccc(-c3ccc(C(=O)O)cc3)cc2cc1C12CC3CC(CC(C3)C1)C2] |
| MM11253 | RAR agonist | 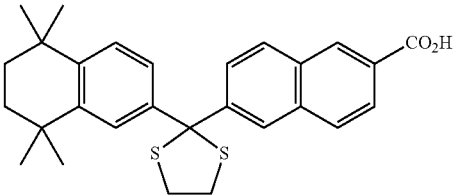 [SMILES: CC1(C)CCC(C)(C)c2cc(C3(c4ccc5cc(C(=O)O)ccc5c4)SCCS3)ccc21] |
| LE135 | RARβ agonist | 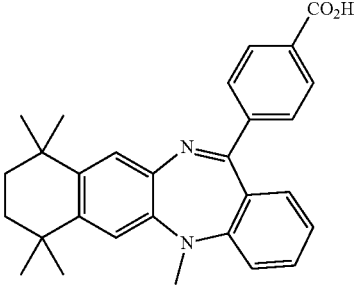 [SMILES: CN1c2cc3c(cc2N=C(c2ccc(C(=O)O)cc2)c2ccccc21)C(C)(C)CCC3(C)C] |
| BMS493 | Pan-RAR inverse agonist | 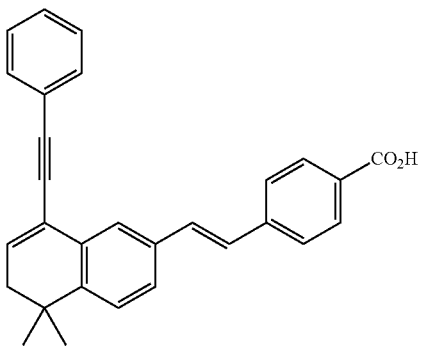 [SMILES: CC1(C)CC=C(C#Cc2ccccc2)c2cc(/C=C/c3ccc(C(=O)O)cc3)ccc21] |

TABLE 1-continued

RAR agonists

| Compound Name | Specificity | Structure |
|---|---|---|
| BMS453 | RARβ agonist<br>RARα or RARγ<br>Antagonist | 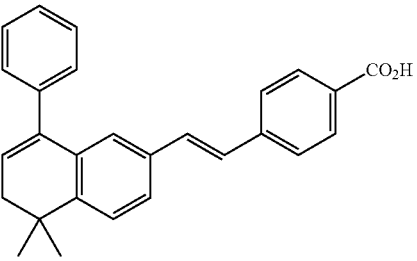 [SMILES: CC1(C)CC=C(c2ccccc2)c2cc(/C=C/c3ccc(C(=O)O)cc3)ccc21] |

In some embodiments, pro-inflammatory type I NKT cell activity is inhibited by one or more RAR agonists selected from the group consisting of ATRA, retinol, 9-cis-RA or 13-cis-RA, tretinoin, AM580, AC55649, CD1530 or Tazarotene. In some embodiments, pro-inflammatory type I NKT cell activity is inhibited by one or more polyolefinic retinoids, such as isoretinoin and acitretin. In some embodiments, pro-inflammatory type 1 NKT cell activity is inhibited by one or more RAR agonists selected from the group consisting of etretinate, acitretin and isotretinoin.

Several embodiments relate to the inhibition of pro-inflammatory type I NKT cell activity by tazarotene, tazarotenic acid or a mixture thereof. Tazarotene is an ethyl ester prodrug that is metabolized to the corresponding free acid, tazarotenic acid. Tazarotene has a rigid ring-locked structure that offers limited conformational flexibility compared to all-trans-retinoic acid, the natural ligand for the retinoic acid receptors (RARs). This structural change confers tazarotenic acid with specificity for the RARs and selectivity for RARβ and RARγ.

Examples of RAR agonists further include esters of cis- and trans-retinoic acids, for example, alkyl esters, such as primary, secondary or tertiary alcohols, including but not limited to: methyl, ethyl, propyl, iso-propyl, butyl, iso-butyl, hexyl, heptyl, ethylhexyl, octyl, nonyl, lauryl, oleyl, stearyl, hydroxyethyl, hydroxypropyl, benzyl, alpha-methylbenzyl, alpha-propylphenyl, amyl, iso-amyl, anisyl, cetyl, menthyl, cinnamyl, pinacol, furyl, or myristyl.

Pharmaceutically acceptable salts of RAR agonists can also be used to inhibit type I NKT cell activity. Compounds disclosed herein which possess a sufficiently acidic, a sufficiently basic, or both functional groups, and accordingly can react with any of a number of organic or inorganic bases, and inorganic and organic acids, to form a salt.

Examples of acids that may be used to form acid addition salts from RAR agonists with basic groups include inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Examples of bases that may be used to form base addition salts from RAR agonists with acidic groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl) amine; N-methyl-D-glucamine; and amino acids such as arginine, lysine, and the like.

As used herein, the term "patient" refers to the recipient of a therapeutic treatment and includes all organisms within the kingdom animalia. In preferred embodiments, the animal is within the family of mammals, such as humans, bovine, ovine, porcine, feline, buffalo, canine, goat, equine, donkey, deer and primates. The most preferred animal is human.

As used herein, the terms "treat" "treating" and "treatment" include "prevent" "preventing" and "prevention" respectively.

As used herein the term "an effective amount" of an agent is the amount sufficient to treat, inhibit, or prevent liver damage resulting from pro-inflammatory type 1 NKT cell activity.

Some embodiments relate to pretreatment of patients with a sulfatide and/or an RAR agonist prior to clinical manifestation of ALD. In several embodiments, patients are treated with an effective amount of sulfatide and/or an RAR agonist prior to binge alcohol consumption. In some other embodiments, patients are treated with an effective amount of sulfatide and/or an RAR agonist from about 0.5 hour to about 18 hours prior to binge alcohol consumption. In some other embodiments, patients are treated with an effective amount of sulfatide and/or an RAR agonist during a period of chronic alcohol consumption.

In some embodiments, the specific amount of RAR agonist administered to a patient will vary depending upon the disease or condition being treated, as well as the age, weight and sex of the patient being treated. Generally, to achieve such a final concentration in, e.g., the intestines or blood, the amount of RAR agonist in a single dosage composition of the present embodiments will generally be about 0.1 milligrams to about 100 milligrams, preferably about 2.0 milligrams to about 60 milligrams, more preferably about 20 milligrams to about 50 milligrams. Examples of suitable doses include: between about 0.1 to about 10 mg/day; between about 0.5 to about 2 mg/day; between about 0.01-100 mg/day; between about 1 to about 50 mg/day; between about 0.1 mg/day to about 1.0 mg/day; between about 1.0 mg/day and about 5.0 mg/day; between about 5.0 mg/day and about 10.0 mg/day; between about 10.0 mg/day and about 15 mg/day; between about 15.0 mg/day and about 20.0 mg/day; between about 20.0 mg/day and about 25.0 mg/day; between about 30.0 mg/day and about 35.0 mg/day; between about 35.0 mg/day and about 40.0 mg/day; between about 40.0 mg/day and about 45.0 mg/day; between about 45.0 mg/day and about 50.0 mg/day; between about 50.0 mg/day and about 55.0 mg/day; between about 55.0 and about 60.0 mg/day; between about 60.0 mg/day and about 65.0 mg/day; between about 65.0 mg/day and about 70.0 mg/day; between about 70.0 mg/day and about 75.0 mg/day; between about 75.0 mg/day and about 80.0 mg/day; between about 80.0 mg/day and about 85.0 mg/day; between about 85.0 and about 90.0 mg/day; between about 85.0 mg/day and about 90.0 mg/day; between about 90.0 mg/day and about 95.0 mg/day; and between about 95.0 mg/day and about 100.0 mg/day. Obviously, the exact dosage will vary with the disease or disorder being treated, the preferred ranges being readily determinable.

When tazarotene is orally administered to effect a reduction in type I NKT cell activity, the daily dosage of tazarotene preferably is in a range of about 0.3 mg/day to about 7 mg/day or about 8 mg/day, more preferably in a range of about 0.6 mg/day to about 6.5 mg/day or about 7 mg/day. In some embodiments, orally administered tazarotene is administered in daily dosages of tazarotene including 0.4 mg/day, 0.75 mg/day, 1.5 mg/day, 2.8 mg/day, 3 mg/day, 4.5 mg/day, 6 mg/day and 6.3 mg/day.

In accordance with the embodiments, RAR agonist can be administered to alleviate a patient's symptoms, or can be administered to counteract a mechanism of the disorder itself. In certain embodiments, RAR agonist may be administered as a prophalactic measure. In some embodiments multiple doses of RAR agonist is administered. It will be appreciated by those of skill in the art that these treatment purposes are often related and that treatments can be tailored for particular patients based on various factors. These factors can include the age, gender, or health of the patient, and the progression of autoimmune or immune related disease or disorder. The treatment methodology for a patient can be tailored accordingly for dosage, timing of administration, route of administration, and by concurrent or sequential administration of other therapies.

In some embodiments, one or more RAR agonist compounds can be administered alone or in combination with another therapeutic compound. For example, one or more RAR agonist compounds can be administered in combination with a sulfatide. Any currently known therapeutic compound used in treatment of the alcoholic liver disease, inflammatory disease, autoimmune disease or reperfusion injury can be used. In some embodiments, RAR agonist can be administered in combination with hydrogen sulfide ($H_2S$). In some embodiments RAR agonist can be administered in combination with antioxidants. In some embodiments RAR agonist can be administered in combination with, for example, corticosteroids, biologics (e.g. anti-TNF-alpha and anti-IL-6), immunomodulators (e.g. RU-486), disease modifying anti-rheumatic drugs (DMARDS, such as leflunomide), COX-2 inhibitors (celecoxib), non-steroidal anti-inflammatory drugs (NSAIDS, such as naproxen), oral anti-diabetic (OAD, such as metformin or sitaglipten), GLP-1 agonists, insulin, PPAR agonists/antagonists, EGF mediators (anti-cancer agents), other agents effective to treat hepatic cancers, cell-based therapies for liver cancers; interferons (IFN) for Hepatitis C, multiple sclerosis or lupus erythematosus; and LFA-1 antagonists.

The RAR agonist compounds and sulfatide compounds described herein may be used as an active ingredient incorporated into a pharmaceutical composition. In some embodiments the pharmaceutical composition may comprise a single active ingredient. In some embodiments the pharmaceutical composition may comprise two, three, four, five or more active ingredients. All modes of administration are contemplated, for example, orally, rectally, parenterally, topically, or by intravenous, intramuscular, intrasternal or subcutaneous injection or in a form suitable by inhalation. The formulations may, where appropriate, be conveniently presented in discrete dosage units and may be prepared by any of the methods well known in the art of pharmacy. The active ingredients will ordinarily be formulated with one or more pharmaceutically acceptable excipients in accordance with known and established practice. Thus, the pharmaceutical composition can be formulated as a liquid, powder, elixir, injectable solution, suspension, suppository, etc.

Active ingredients according to some embodiments can be formulated for administration for oral administration as tablets, hard gelatin capsules, soft gelatin capsules, comprising the active in the form of a powder, a blend with excipients, a liquid or solution, a suspension, a solid solution. Active ingredients according to some embodiments can be formulated for administration for intra-oral administration (sublingual or buccal) as a solid dosage form rapidly dissolving or effervescent tablets, thin films, buccal wafers, or as a liquid or semi-solid form, such as a gel, solution, emulsion, suspension. Active ingredients according to some embodiments can be formulated for administration for injection as an aqueous or non-aqueous solution, suspension or emulsion. Oil-based solutions and suspensions comprise mixtures of natural and or synthetic oils such as soybean oil, cotton seed oil, mineral oil, sesame oil, castor oil, hydrogenated vegetable oils, beeswax. Active ingredients according to some embodiments can be formulated for administration for transdermal administration as a cream, a gel, an emulsion, an aqueous-based solution, an oil-based solution, a suspension, a film, a patch, a foam. Active ingredients according to some embodiments can be formulated for administration for intranasal administration as a powder, suspension, solution, emulsion. Active ingredients according to some embodiments can be formulated for administration for pulmonary delivery as a micronized powder. Oral administration is associated with first pass metabolism as well as induction of metabolizing enzymes. Thus dosage strength and dosing regimen of oral administered retinoic acids may be tailored for optimal effect. Alternative routes of delivery, e.g. sublingual, buccal, injection, pulmonary and transdermal, may be a preferred over oral administration. Alternative routes of administration, such as those as described, avoid first pass metabolism and GI absorption, demonstrate less enzyme induction and provide steady repeat dose pharmacokinetics.

Pharmaceutical formulations according to the present embodiments may be immediate release or modified release (e.g., sustained release, pulsatile release, controlled release, delayed release, slow release). Because it is immediately active, pharmacological amounts of orally administered Retinoid isomers may have side effects. These side effects have been a serious limitation to the use of oral retinoids in therapy. Although topically applied retinoids carry little teratogenic liability there are other toxicities associated with this route of administration that limit their use including skin irritation. A major reason for both oral and topical toxicity is that the retinoids are totally and immediately available upon administration. A process whereby a retinoid can be made available in vivo more slowly and more continuously would avoid peaks and valleys in the availability of the retinoid thereby providing an effective in vivo level of the compound over a more prolonged period of time and also avoiding or substantially reducing the toxicities that often result from the sudden availability of excessive amounts of the substance. An oil based injectable formulation of retinol, ester of retinol, and in particular a fatty ester of retinol, retinoic acid or a retinoic acid ester could be administered intra-muscularly on a weekly basis and provide a systemic slow-release delivery, according to such principles.

In some embodiments, preparation of all-trans-retinoic acid tert-butyl ester is as follows. To a solution of all-trans retinoic acid (100 mg, 0.33 mmol) in anhydrous ether was added oxalyl chloride (42.3 mg, 0.333 mmol) at 0.degree. C. and stirred at that temperature for 30 minutes and pyridine (28.7 mg, 0.363 mmol), 2-methyl-2-propanol (26.8 mg, 0.363 mmol) was added and stirred at room temperature in dark after which time the reaction was complete as indicated by the TLC. The reaction mixture was then quenched with water and extracted with ether (3.times.10 ml), saturated sodium bicarbonate solution (3.times.5 ml) and again with water (3.times.5 ml), dried (MgSO.sub.4) and evaporated. The thick residue was redissolved in hexane and applied on silica Sep-Pak cartridge (2 g). Elution with hexane/ethyl acetate (9.7:0.3) provided the butyl ester of retinoic acid. Final purification was achieved by HPLC (10 mm.times.25 cm Zorbax-Sil column, 4 mL/min) using hexane/isopropanol (90:10) solvent system. Pure all-trans retinoyl butyrate 2 (98 mg, 82.6%) was eluted at as a thick oil.

Some embodiments relate to formulation of butyl-retinoic ester for injection as described below. 10 g butyl-retinoic ester solution is dissolved in a mixture of 73 g cottonseed oil containing 0.1 g butylated hydroxyanisole, and 10 g benzyl alcohol at slightly elevated temperature and with high-shear mixing under aseptic conditions. The mixture is sterile filtered and filled into a syringe for later use. To be administered by intramuscular injection. Some embodiments relate to formulation of retinol palmitate in cottonseed oil as above for intramusculat injection.

Some embodiments relate to formulation of an oral dosage form of one or more active ingredient of the present embodiments as described below. 10 g retinoic acid is dissolved in a mixture of beeswax, butylated hydroxyanisole, edetate disodium, hydrogenated soybean oil flakes, hydrogenated vegetable oils and soybean oil alcohol at slightly elevated temperature and with high-shear mixing. The mixture is sealed into soft-gelatin capsules at dosage strengths of 2 mg, 5 mg and 10 mg for oral administration.

Some embodiments relate to formulation of a bioadhesive buccal tablet containing one or more active ingredient of the present embodiments. A blend of excipients is prepared containing 24% active ingredient, 21% HPMC, 18% Corn Starch, 24% Lactose, 1% Silica, 2.5% Polycarbophil (Noveon), 7.5% Carbomer 974P, 1.2% Talc and 0.7% Magnesium Stearate. The blend was pressed into tablets approximately 1 cm in diameter.

Some embodiments relate to formulation of a sublingual film containing one or more active ingredient of the present embodiments. The following are mixed in 50 g water: 3 g Methocel E5, 5 g Methocel E50, 1 g Klucel, 1 g Maltodextrin, 1 g citric acid, 3 g sucralose, 5 g Orange flavor, 0.2 g paraben, 0.1 edetate sodium and 5 g Sorbitol. 1 g retinoic acid is added and the mixture is degassed with stirring. The composition is thinly spread across a polyester film support and allowed to dry in the air in the absence of any direct light to avoid degradation. The film is then cut to size to generate doses of 2 to 10 mg.

Some embodiments relate to a kit, which may include one or more sulfatides, RAR agonists or any combination thereof, preferably as a pharmaceutical composition. In some embodiments, cis-tetracosenoyl is provided in a pharmaceutically acceptable carrier. In some embodiments, ATRA is provided in a pharmaceutically acceptable carrier. In some embodiments, tazarotene is provided in a pharmaceutically acceptable carrier. In several embodiments, hydrogen sulfide ($H_2S$) may optionally be provided. In several embodiments, one or more antioxidants may optionally be provided. In several embodiments, kits may further comprise suitable packaging and/or instructions for use. Kits may also comprise a means for the delivery of the one or more sulfatides, RAR agonists or any combination thereof, such as an inhaler, spray dispenser (e.g., nasal spray), syringe for injection, needle, IV bag or pressure pack for capsules, tables, suppositories. The one or more sulfatides, RAR agonists or any combination thereof can be in a dry or lyophilized form or in a solution, particularly a sterile solution. When in a dry form, the kit may comprise a pharmaceutically acceptable diluent for preparing a liquid formulation. The kit may contain a device for administration or for dispensing the compositions, including, but not limited to, syringe, pipette, transdermal patch, or inhalant. Some embodiments relate to kits that contain sufficient dosages of the compounds or composition to provide effective treatment for an individual for an extended period, such as a week, 2 weeks, 3 weeks, 4 weeks, 6 weeks, or 8 weeks or more.

In one example embodiment, a 70 kg adult patient at risk of chemical liver damage from prescription drugs or drugs of abuse is given a daily i.m. injection of 7 mg tazarotene in 1.0 ml phosphate buffered saline to treat liver damage. This dosage can be adjusted based on the results of the treatment and the judgment of the attending physician. Treatment is preferably continued for at least about 1 or 2 weeks, preferably at least about 1 or 2 months, and may be continued on a chronic basis.

In another example embodiment, a 70 kg adult patient at risk of chemical liver damage from prescription drugs or drugs of abuse is given an oral dose of an RAR agonist sufficient to inhibit activity of type 1 NKT cells. Liver damage may be monitored by analysis serum liver enzyme levels. The dosage of RAR agonist can be adjusted based on the results of the liver function test and the judgment of the attending physician. Treatment is preferably continued for at least about 1 or 2 weeks, preferably at least about 1 or 2 months, and may be continued on a chronic basis. In some embodiments the duration of treatment coincides with duration of behavior placing the patient at risk for chemical liver damage. In some embodiments, the RAR agonist is selected from the group consisting of ATRA and tazarotene. In some embodiments, the patient is further administered a dose of sulfatide sufficient to activate type II NKT cells.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The present embodiments should therefore not be limited by the above described embodiment, method, and examples, but by all embodiments and methods within the scope and spirit of the present embodiments.

The following Examples are presented for the purposes of illustration and should not be construed as limitations.

Example 1

Sulfatide Mediates Inhibition of Type I NKT Cells while Activating Sulfatide/CD1d-Tetramer+ Cells A dose of 20 μg sulfatide was injected intraperitoneally in mice. Following sulfatide injection, MNCs from liver were isolated and labeled with CFSE. The cells were cultured with αGalCer (10 ng/ml) for 96 hours in the presence or absence of 10 ng/ml cytokine IL-2. Cells were cultured with 10 ng/ml IL-12 alone as a control. Following culture, cells were harvested, stained with anti-TCRβ mAb and αGalCer/CD1d-tetramers, FACs sorted and CFSE dilution analysis was performed on αGalCer/CD1d-tetramer$^+$ (type I NKT) cells. See FIG. 1A. As shown in FIG. 1B, after sulfatide administration, type I NKT cells fail to proliferate in response to an in vitro challenge with αGalCer.

Liver cells isolated from PBS or 20 μg sulfatide injected mice were sorted into sulfatide/CD d-tetramer+ and tetramer-populations and stained for intracytoplasmic IFN-γ+. As shown in FIG. 1C, sulfatide-injected mice have the greatest % IFN-γ positive cells.

Administration of sulfatide results in both the inhibition of type I NKT cell proliferation and increase in the % IFN-γ positive cells. Not to be bound by a particular theory, it is suggested that sulfatide administration activates both pDC and type II NKT cells which secrete cytokines and chemokines and this interaction results in cDC-mediated inhibition induction in type I NKT cells.

Example 2

Sulfatide Administration Protects Against ConA-Induced Hepatitis

Female C57BL/6 mice were treated with 8.5 mg/kg of Concavalin A (ConA) (dissolved in pyrogen free phosphate buffer saline, PBS) intravenously (i.v.), which induces liver damage similar to that caused by hepatitis. Immediately after ConA injection, mice were injected intraperitonially (i.p.) with 20 μg (1 mg/kg/m) of bovine brain sulfatide or PBS.

Damage to the liver gives rise to telltale abnormalities (suggesting liver disease) detectable by liver function tests. For example, viral hepatitis can cause the alanine amino transferase (ALT) and aspartate amino transferase (AST) enzymes in injured liver cells to spill into the blood stream and increase their level in the blood. To test for liver damage, serum was collected and levels of serum enzymes, ALT and AST, were measured at 0, 6, 12, 24, 48 and 72 hours following Con A or Con A+sulfatide injection. Serum enzyme levels were measured with the help of Laboratory Corporation of America, San Diego, Calif. As shown in FIG. 1e, comparable levels of serum enzymes were observed 6 hours after Con A or Con A+sulfatide injection, however, both ALT and AST serum levels were lower at 12, 24, and 48 hours in mice injected with both ConA and sulfatide. In Con A (●) injected mice, serum ALT and AST peaked around 12 h (ALT≈15.8×10$^3$ IU/L and AST≈22.7×10$^3$ IU/L) and returned to base line by 48 hours. In contrast, following combination of Con A+sulfatide (○) injection, a significant decrease in serum level of ALT and AST (ALT≈2.5×10$^3$ IU/L and AST≈5.4×10$^3$ IU/L) by 12 h was recorded and returned to base line by 24 h. Values are mean±SD of 5 mice per group. P<0.001.

Mice were sacrificed at 12, 24, 48, 72, and 96 hours after treatment and their livers were collected. Liver tissue was fixed in 10% formaldehyde solution and kept at room temperature until use. Histological examination using hematoxylin and eosin (H&E) staining was performed at Pacific Pathology Inc., San Diego, Calif.

As shown in FIG. 1d, H&E staining demonstrated markedly improved hepatic histology in Con A+bovine brain sulfatide treated mice relative to mice treated with Con A alone. Histological examination showed diffuse and massive infiltration and severe necrosis at the indicated time points following Con A injection mice, FIG. 1d, top panels. In contrast, sulfatide+Con A injection was associated with mild injury in terms of less infiltration and less necrosis in the 12 h to 48 h liver sections and histology returned to normal by 72 h, FIG. 1d, bottom panels.

Taken together, results obtained in Example 1 and Example 2 indicate that (a) sulfatide mediates inhibition of type I NKT cells in the liver and (b) sulfatide administration activates sulfatide/CD1d-tetramer+ cells and protects against ConA-induced hepatitis. This indicates that tolerized cDCs and anergic type I NKT cells collectively lead to a significant inhibition of a detrimental inflammatory cascade.

Example 3

Analysis of the Effect of the Immune Response to Hepatic Ischemia and Reperfusion Injury on the Composition of the CD11b+Gr-1+ Cell Population The hepatic ischemia and reperfusion injury model was established as described in Shen X D, Ke B, Zhai Y, et al., CD154-CD40 T-cell costimulation pathway is required in the mechanism of hepatic ischemia/reperfusion injury, and its blockade facilitates and depends on heme oxygenase-1 mediated cytoprotection. Transplantation 2002, 74:315-9, incorporated herein in its entirety, with few modifications.

WT mice and Jα18$^{-/-}$ mice, which lack type I NKT cells but have normal levels of type II NKT cells, (3-5 mice/group) or WT mice (2-3 mice/group) treated 3 hours prior with 20 μg sulfatide/mouse were anesthetized by intraperitoneal injection of 60 mg/kg sodium pentobarbital. After midline laparotomy, an atraumatic clip was applied to the hepatic triad (hepatic artery, portal vein, bile duct) of the 3 cephalad liver lobes. The caudal lobes retained intact blood circulation to prevent intestinal venous congestion. The peritoneum was closed and mice were placed on a heating pad (~37° C.). Ambient temperature ranged between 25-26° C. After 90 min of partial hepatic warm ischemia, the clip was removed, initiating reperfusion, and the abdominal wall was sutured. Mice were euthanized after 6 hours of reperfusion, and blood and cephalad liver lobes were collected. Sham controls underwent the same procedure but without vascular occlusion.

Cell preparation. Leukocytes were isolated from the cephalad liver lobes of the mice using mechanical crushing followed by Percoll gradient separation and RBC lysis as described in Halder R C, Aguilera C, Maricic I, et al., Type II NKT cell-mediated anergy induction in type I NKT prevents inflammatory liver disease. J Clin Invest 2007, 117:2302-12.

Flow cytometry. Leukocytes were suspended in FACS buffer (PBS containing 0.02% $NaN_3$ and 2% FCS), blocked (anti-mouse FcR-γ, BD Pharmingen, San Diego, Calif.) and stained with loaded mCD1d-tetramer-PE or PE-, FITC-, or PE-Cy5-labeled anti-mouse antibodies (BD Pharmingen, San Diego, Calif. or eBioscience Inc., San Diego, Calif.) as indicated. Intracellular cytokine staining (ICCS) of liver mononuclear cells (MNCs) was carried out as described in Halder R C, Aguilera C, Maricic I, et al., Type II NKT cell-mediated anergy induction in type I NKT prevents inflammatory liver disease. J Clin Invest 2007, 117:2302-12. Analysis was performed on a FACSCalibur instrument using CellQuest software (version 4.0.2, BD, Franklin Lakes, N.J.). Gr-$1^{high}$ and Gr-$1^{int}$ populations were gated. See FIG. 2a.

Statistics. Data are expressed as mean±SEM for each group. P<0.005. Statistical differences between groups were evaluated by unpaired, one-tailed Student's t test using GraphPad Prism software (version 5.0a, GraphPad Software Inc., La Jolla, Calif.).

Results. The Gr-$1^{int}$ subset of cells is comprised predominantly of monocytes and myeloid precursors. Following ischemia and reperfusion injury (IRI), Gr-$1^{int}$ cells were increased around 3.5-fold (p<0.005) compared to sham in the livers of WT mice, while no increase was observed following ischemia and reperfusion injury in Jα18$^{-/-}$ mice. See FIG. 2b, top panels. Therefore, the hepatic recruitment of myeloid cell subsets during ischemia and reperfusion injury is dependent on the presence of type I NKT cells, which are lacking in Jα18$^{-/-}$ mice.

When compared to untreated mice, the Gr-$1^{int}$ cell subset was reduced in sulfatide-treated mice by ~50% following IRI. This suggests that the myeloid cell recruitment activity of type I NKT cells was reduced following sulfatide treatment.

Figure 2B:
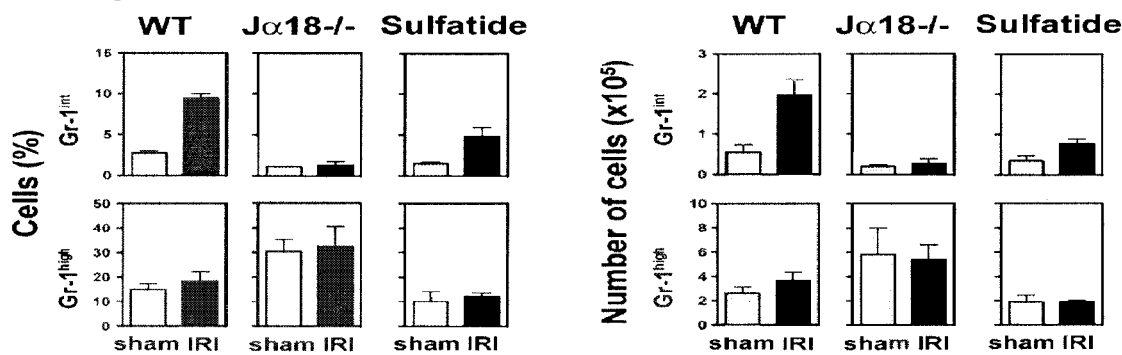
Figure 2C:
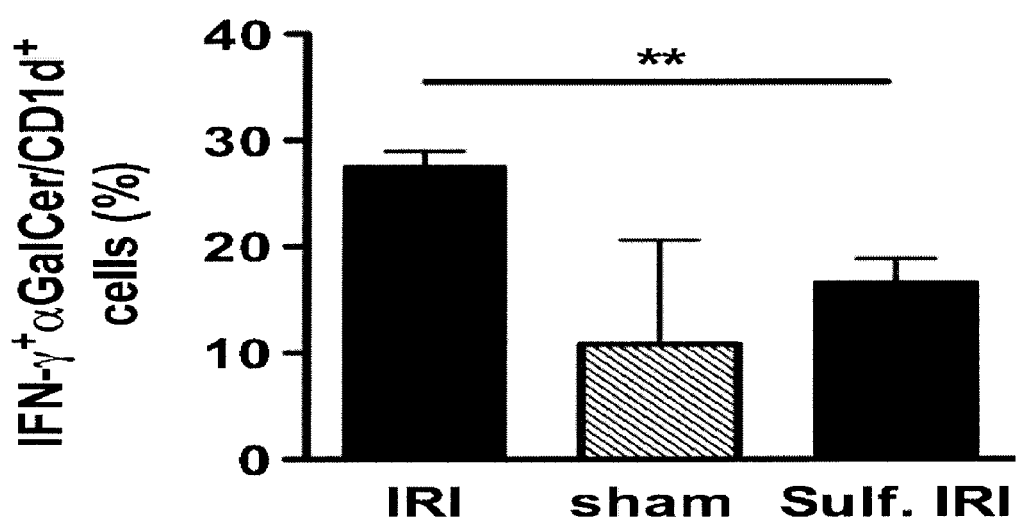

The Gr-$1^{high}$ cell subset, which mainly consists of granulocytes, did not differ significantly between livers of sham controls and ischemia and reperfusion injury-induced mice. FIG. 2b, bottom panels.

Example 4

Sulfatide Administration Prior to Ischemia and Reperfusion Injury Induction Significantly Inhibits IFN-γ Secretion by Type I NKT Cells.

One group of WT mice (n=3) was injected with sulfatide (20 μg/mouse i.p.) 3 hrs prior to ischemia induction (Sulf. IRI), the other groups (IRI (n=3), sham (n=2)) were not pretreated. Hepatic ischemia and reperfusion injury (90 min of ischemia and 6 hrs of reperfusion) and sham surgery were performed as described in Example 3.

Cell preparation. Leukocytes were isolated from murine cephalad liver lobes, using mechanical crushing followed by Percoll gradient separation and RBC lysis as described in Halder R C, Aguilera C, Maricic I, et al., Type II NKT cell-mediated anergy induction in type I NKT prevents inflammatory liver disease. J Clin Invest 2007, 117:2302-12.

Flow cytometry. Leukocytes were suspended in FACS buffer (PBS containing 0.02% $NaN_3$ and 2% FCS), blocked (anti-mouse FcR-γ, BD Pharmingen, San Diego, Calif.) and stained with αGalCer loaded mCD1d-tetramer-PE anti-mouse antibodies (BD Pharmingen, San Diego, Calif. or eBioscience Inc., San Diego, Calif.). Analysis was performed on a FACSCalibur instrument using CellQuest software (version 4.0.2, BD, Franklin Lakes, N.J.).

Statistics. Data are expressed as mean±SEM for each group. P<0.01. Statistical differences between groups were evaluated by unpaired, one-tailed Student's t test using GraphPad Prism software (version 5.0a, GraphPad Software Inc., La Jolla, Calif.).

Results. After ischemia and reperfusion injury induction, type I NKT cells show increased IFN-γ production compared to type I NKT cells from sham surgery, while administration of sulfatide 3 hrs prior to ischemia and reperfusion injury significantly reduced IFN-γ secretion by type I NKT cells. See FIG. 2c.

Example 5

Suppression of Type I NKT Cells Results in Reduced Hepatic Necrosis Following IRI Purified bovine myelin-derived sulfatide (>90% pure), purchased from Matreya Inc., Pleasant Gap, Pa., was dissolved in vehicle (0.5% polysorbate-20 (Tween-20) and 0.9% NaCl solution) and diluted in PBS. Groups of BL/6 mice (WT sulfatide) and Jα18$^{-/-}$ mice (Jα18$^{-/-}$ sulfatide) were treated with sulfatide (20 μg/mouse) intraperitoneally 3 to 48 hrs prior to ischemia induction or sham surgery. Hepatic ischemia and reperfusion injury and sham surgery were conducted as described in Example 3 on sulfatide treated and untreated WT and Jα18$^{-/-}$ mice. Following 90 min of ischemia and 24 hrs of reperfusion, liver tissues (cephalad lobes) were fixed in 10% formalin, embedded in paraffin and sections were stained with hematotoxylin and eosin for histological analysis (IDEXX Laboratories Inc., Westbrook, Me.).

WT mice pretreated with sulfatide (WT sulfatide) and Jα18$^{-/-}$ mice developed only minimal or no hepatic necrosis after IRI, whereas large necrotic areas were found in the cephalad liver lobes of the untreated (WT) mice. See FIG. 4, top panels. Sham controls showed no necrosis. See FIG. 4, bottom panels. The histological analysis indicated that necrosis following IRI is reduced in the livers of mice lacking type 1 NKT cells (Jα18$^{-/-}$ mice) and mice in which the activity of type 1 NKT cells is suppressed by sulfatide treatment.

Example 6

Induction of Alcoholic Liver Disease in WT and Type 1 NKT Cell-Depleted (Jα18−/−) Mice Following acclimatization with nutritionally adequate Lieber-DeCarli liquid diet for a week, 6-8 week old male C57BL/6J mice (B6) and Jα18−/− mice, which lack type 1 NKT cells but not type 2 NKT cells, were given free access to a liquid diet containing 5% ethanol or an isocaloric dextrin maltose-containing diet (Bio-Serv, NJ). Precautions were taken to prepare the diet fresh every day using autoclaved water in sterilized feeders, changing feed daily.

B6 and Jα18−/− mice receiving the ethanol-containing diet were separated into two groups, the chronic ethanol feeding group and the chronic plus binge ethanol feeding group. Mice in the chronic ethanol feeding group were fed liquid diet containing 5% ethanol for up to 4-5 weeks. Mice in the chronic plus binge ethanol feeding group were fed liquid diet containing 5% ethanol for 10 days followed by (on day 11) a single high dose of gavaged ethanol (5 g/kg body weight). Mice in the control group were gavaged with isocaloric dextrin maltose. Following gavage, mice were kept on a temperature controlled warm pad and monitored.

Though initially slow moving, most mice receiving the high dose of gavaged ethanol regained normal behavior within hours. Mice were euthanized 8-9 hr after gavage.

Figure 9A:
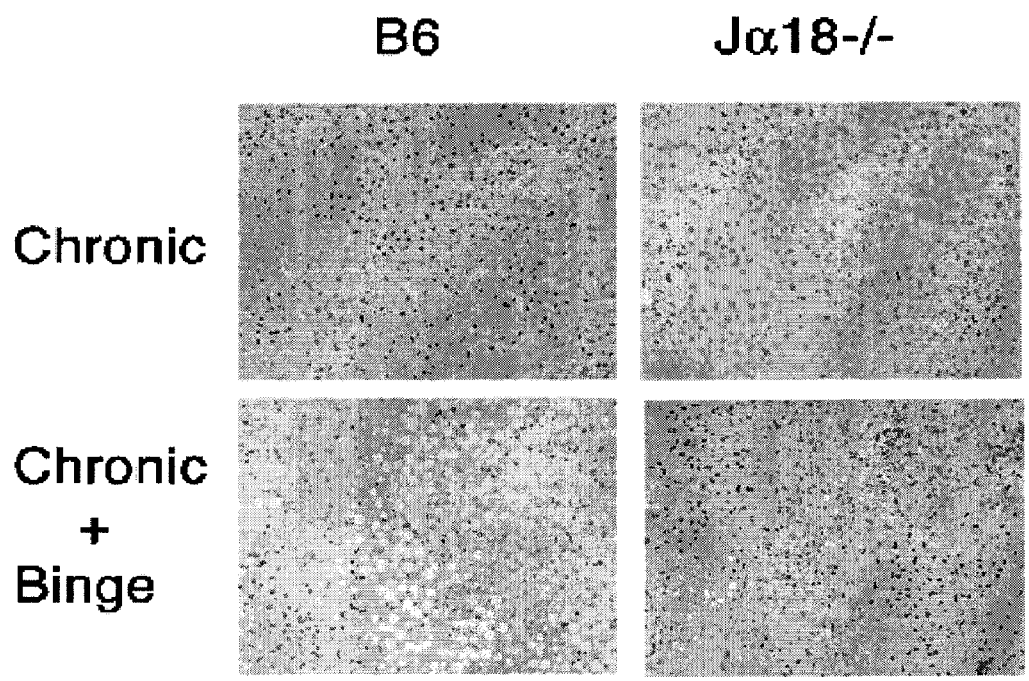
FIG. 9a shows representative micrographs (X200) of H&E stained liver tissue harvested from male BL/6 and Jα18-/- mice following chronic (10 days 5% ethanol in liquid Lieber-DeCarli diet) or chronic plus binge feeding (ten days of chronic feeding of liquid diet followed by a single gavage of 5 g/kg ethanol).

H&E staining was performed on Liver lobe tissue obtained from ethanol-fed male B6 and Jα18−/− mice following either 10 days or 4-5 weeks of chronic ethanol feeding or chronic plus binge ethanol feeding. As shown in FIG. 9a (top panels), histopathological analysis did not show liver damage in either B6 or Jα18−/− mice subjected to chronic ethanol feeding for 10 days. Further, no liver damage was observed by histopathological analysis of the liver tissue of B6 and Jα18−/− mice subjected to chronic ethanol feeding for 4-5 weeks (data not shown). Histopathological analysis of liver tissue from B6 mice subjected to chronic plus binge ethanol feeding, however, showed significant damage. See FIG. 9a, bottom left panel. While liver tissue from Jα18−/− mice subjected to chronic plus binge ethanol feeding showed relatively little damage. See FIG. 9a, bottom right panel.

Figure 9B:
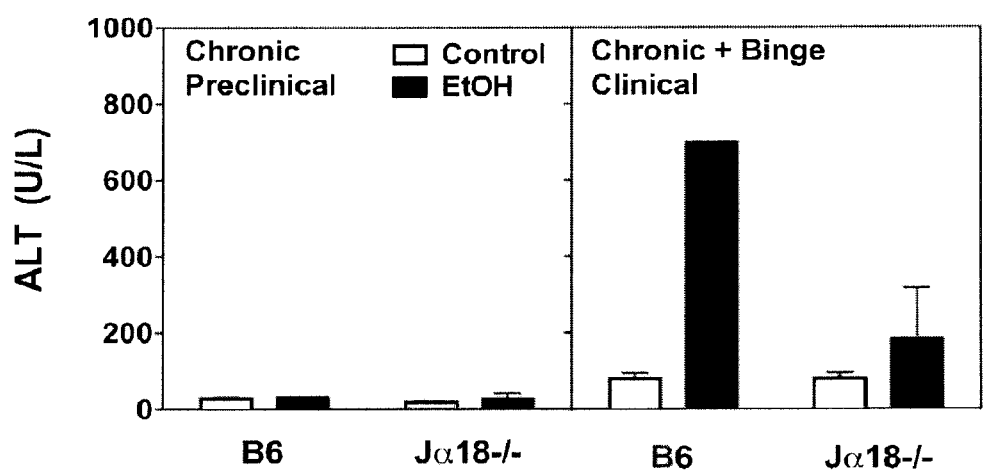
FIG. 9b shows graphs depicting serum ALT levels in control or ethanol fed male BL/6 or Jα18-/- mice following chronic or chronic plus binge feeding.

Serum ALT levels were measured in control B6 and Jα18−/− mice and ethanol fed B6 and Jα18−/− mice following either 10 days or 4-5 weeks chronic ethanol feeding and chronic plus binge feeding. As shown in FIG. 9b, left panel, chronic ethanol did not lead to significant elevation of serum ALT levels. Serum ALT levels were significantly increased in B6 mice subjected to chronic plus binge ethanol feeding, and were increased to a lesser extent in Jα18−/− mice subjected to chronic plus binge ethanol feeding compared to control. See FIG. 9b, right panel.

Maximum liver damage (compared to ethanol-free controls), as exemplified by histology or ALT/AST serum levels, was observed in B6 and Jα18−/− mice 6-8 hrs following high dose ethanol gavage. Between the groups receiving chronic plus binge ethanol feeding, Jα18−/− mice, which lack type 1 NKT cells exhibited less liver damage.

Since chronic ethanol feeding for 10 days or for 4-5 weeks did not lead to any significant liver damage as exemplified by histopathological analysis and no significant change in serum ALT/AST levels, this is referred to pre or subclinical phase ALD. Clinical phase ALD was induced following a second step chronic-binge alcohol feeding.

Liver mononuclear cells (MNCs) were isolated from groups (4 in each) of male B6 and Jα18−/− mice following 5 weeks of feeding with either a liquid Lieber-Decarli diet containing 5% ethanol (chronic ethanol feeding) or a control diet containing a similar number of calories. The isolated liver MNCs were stained with various cell surface antibodies and analyzed by flow cytometry. An accumulation of activated type I NKT cells and CD11b+Gr-1+ myeloid cells was observed in the livers of B6, but not Jα18−/−, mice in the preclinical ALD phase. See FIG. 5.

Example 7

Prevention of Alcohol-Induced Liver Injury by Sulfatide or all-Trans Retinoic Acid (ATRA)

Groups of 7-week-old B6 (WT) and Jα18−/− male mice were injected (i.p.) with: 20 micrograms/mouse sulfatide at days 1 and 10; 0.3 milligrams/mouse ATRA at days 6-10, or vehicle/DMSO and were fed either a liquid diet containing 5% ethanol for 10 days followed by (on day 11) a single high dose of gavaged ethanol (5 g/kg body weight) (chronic plus binge ethanol feeding group) or an isocaloric dextrin maltose-containing diet followed by an isocaloric gavage of with dextrin maltose (control group). The mice were euthanized 6-8 hours following gavage and serum and liver tissue was harvested.

Figure 6:
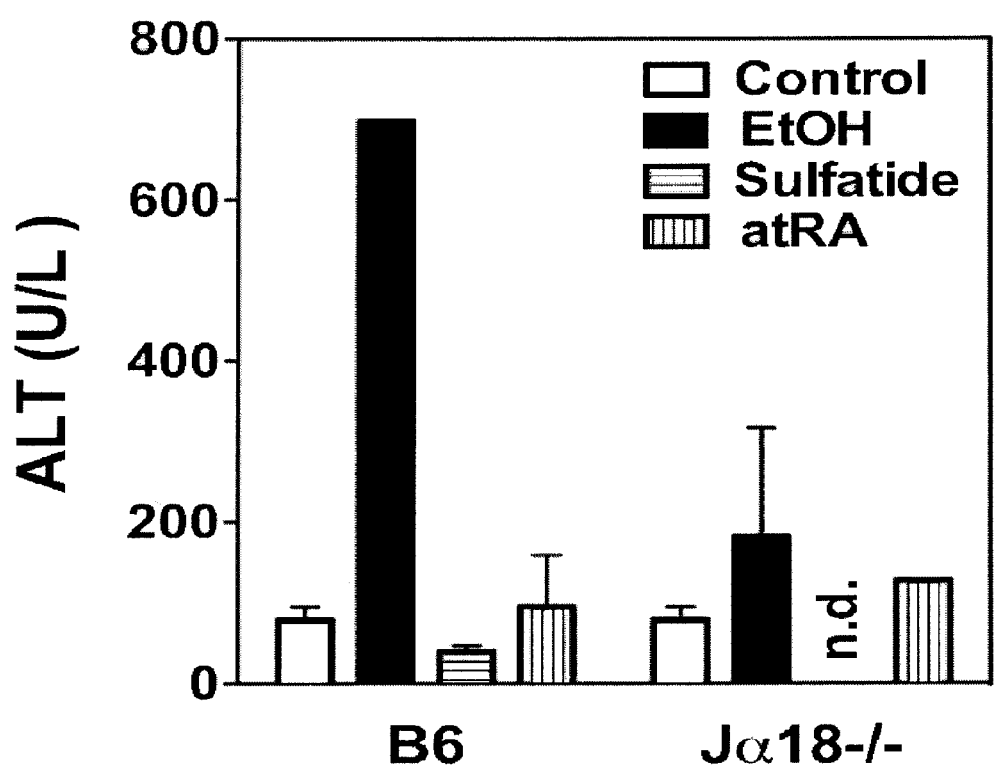
FIG. 6 shows a bar graph depicting serum ALT levels in WT (B6) and Jα18$^{-/-}$ mice injected (i.p.) with 20 micrograms/mouse sulfatide (d-1 & d10) (bars shaded with horizontal lines (Sulfatide)), 0.3 milligrams/animal ATRA (d6 through d10) (bars shaded with vertical lines (atRA)) or vehicle/DMSO (solid shaded bars (EtOH)) and fed Lieber-DeCarli liquid diet containing alcohol. The control groups (unshaded bars) were fed an isocaloric control diet. P values <0.05.

Serum ALT levels were determined for each group of mice. As shown in FIG. 6, serum ALT levels were significantly increased in vehicle/DMSO injected B6 mice subjected to chronic plus binge ethanol feeding (black bar), while the serum ALT levels in chronic plus binge ethanol fed B6 mice receiving either sulfatide (horizontally-striped bar) or ATRA (vertically-striped bar) injections were similar to those of control fed B6 mice (unshaded bar). Serum ALT levels were increased in vehicle/DMSO injected Jα18−/− mice subjected to chronic plus binge ethanol feeding (black bar) compared to control fed Jα18−/− mice (unshaded bar), however, vehicle/DMSO injected Jα18−/− mice subjected to chronic plus binge ethanol feeding had reduced serum ALT levels compared to vehicle/DMSO injected B6 mice subjected to chronic plus binge ethanol feeding. See FIG. 6.

Figure 7:
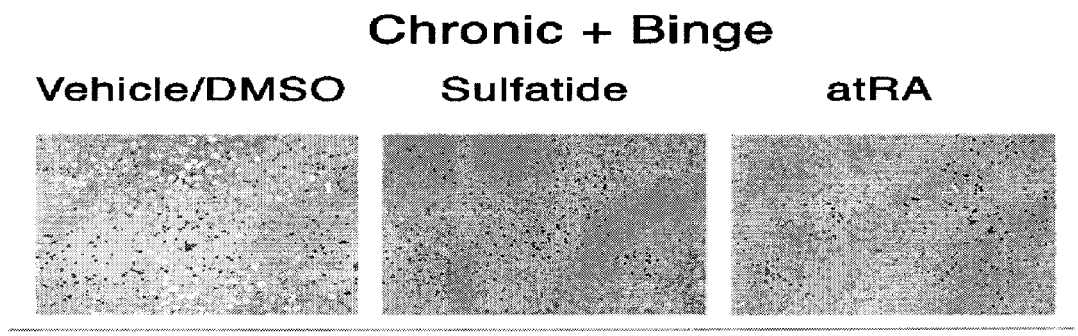
FIG. 7 show representative micrographs (X200) of liver tissue harvested from vehicle/DMSO, sulfatide and ATRA treated mice following chronic plus binge ethanol feeding. Liver tissue from vehicle/DMSO mice shows evidence of hepatic steatohepatitis (fatty liver disease), while liver tissue obtained from sulfatide and ATRA treated mice appears relatively normal.

Histological examination for hepatic steatohepatitis (fatty liver disease) was performed on liver tissue harvested from vehicle/DMSO, sulfatide or ATRA injected B6 mice following chronic plus binge ethanol feeding. As shown in FIG. 7, liver tissue from the vehicle/DMSO injected B6 mice showed significant signs of damage following chronic plus binge ethanol feeding. Liver tissue obtained from sulfatide or ATRA injected B6 mice, however, shows little sign of fatty liver disease.

Histological and serum liver enzyme analysis suggests that administration of either sulfatide or the retinoic acid receptor (RAR) agonist, ATRA, can protect against liver damage caused by excessive alcohol consumption.

Example 8

Inhibition of Type I NKT Cell Proliferation by ATRA

Figure 8A:
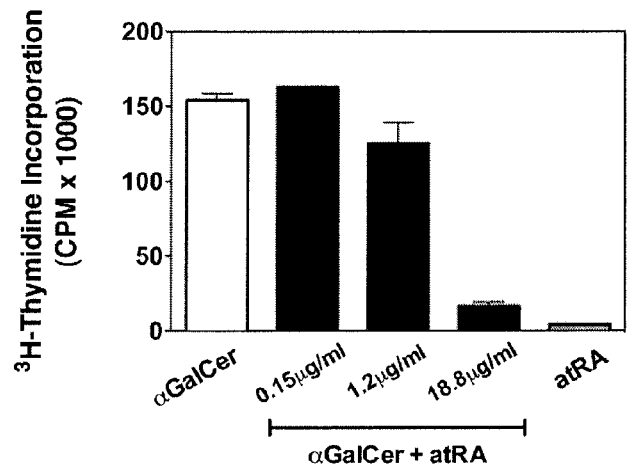
FIG. 8a shows a bar graph depicting proliferation (as measured by [$^3$H]-thymidine incorporation) of freshly isolated type I NKT splenic cells incubated in αGalCer alone, ATRA alone or in αGalCer with increasing levels of ATRA.
Figure 8B:
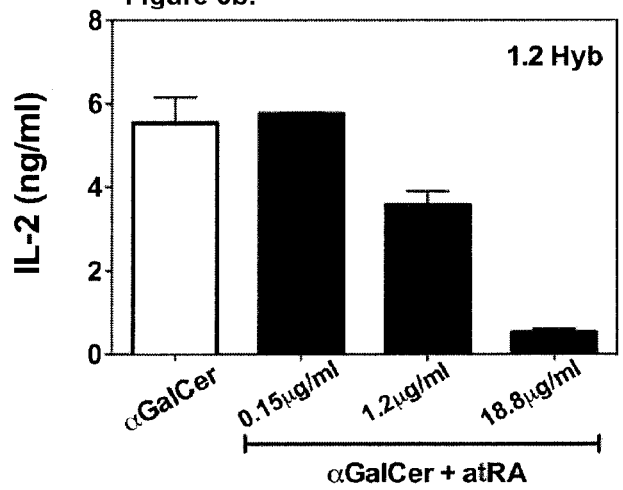
FIG. 8b shows a graph depicting the level of IL-2 cytokine secretion by a type I NKT cell (Hy1.2) in response to αGalCer alone or αGalCer and increasing ATRA levels.

Type I NKT cells were isolated from the spleens of naïve B6 mice and cultured in vitro with [$^3$H]-thymidine and an optimal concentration of αGalCer alone, an optimal concentration of αGalCer plus 0.15 μg/ml, 1.2 μg/ml, or 18.8 μg/ml ATRA, or ATRA alone. Proliferation of the type 1 NKT cells was measured by [$^3$H]-thymidine incorporation. As shown in FIG. 8a, cell proliferation was similar for type 1 NKT cells grown in 0.15 μg/ml ATRA and αGalCer or αGalCer alone, while, by comparison, proliferation was reduced for type 1 NKT cells grown in 1.2 μg/ml or 18.8 g/ml ATRA and αGalCer. The greatest inhibition of αGalCer-induced type 1 NKT cell proliferation was observed for 18.8 μg/ml ATRA. No or minimal proliferation was observed for type 1 NKT cells grown in ATRA alone.

Example 9

Inhibition of Type I NKT Cell Activity by ATRA

The affect of ATRA on IL-2 cytokine secretion by a type I NKT cells in response to an in vitro challenge with αGalCer was tested by co-culturing NKT cells (Hy1.2) and irradiated antigen-presenting cells (APCs) in vitro with an optimal concentration of αGalCer in the presence or absence of ATRA (0.15 μg/ml, 1.2 μg/ml, or 18.8 μg/ml) for a period of 16 hours. Supernatants were collected and secreted IL-2 levels were measured using IL-2 sandwich ELISA.

IL-2 secretion levels were not significantly affected by 0.15 μg/ml ATRA, however, significant reductions in IL-2 secretion was observed for type I NKT cells cultured in the presence of 1.2 μg/ml or 18.8 μg/ml ATRA. The greatest reduction in IL-2 secretion was achieved by 18.8 μg/ml ATRA. See FIG. 8b.

Figure 8C:
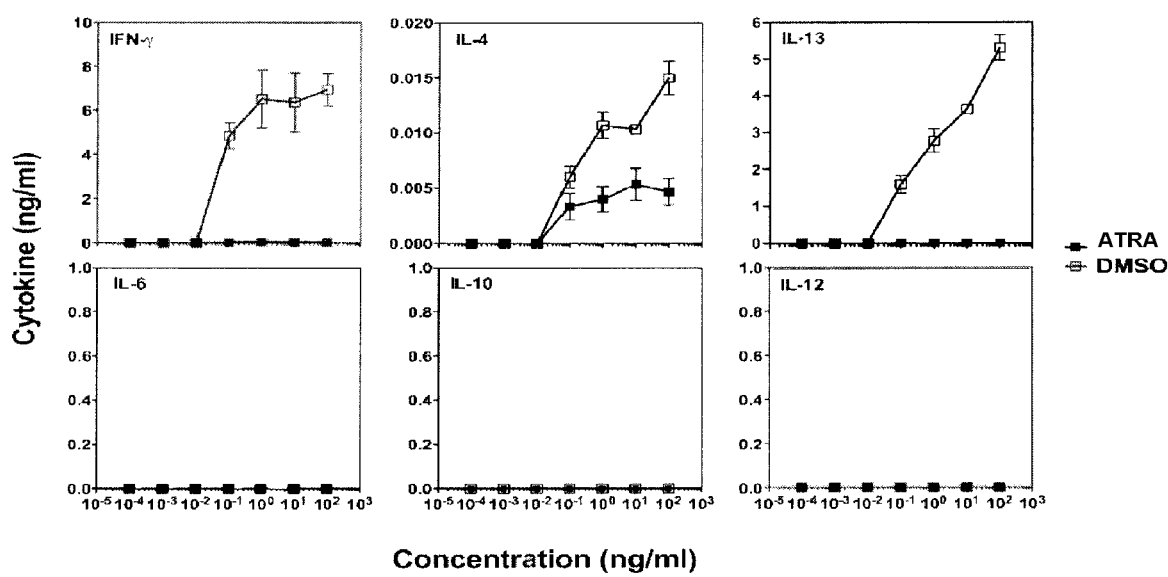
FIG. 8c shows graphs depicting the levels of IFN-γ, IL-4, IL-13, IL-6, IL-10 and IL-12 cytokine secretion by liver type I NKT cells harvested from mice injected with DMSO or ATRA and incubated with αGalCer in vitro. The data shown is representative of 2 individual experiments.

Functional changes in type I NKT cells following ATRA administration were further tested. In two independent experiments, groups of Black 6 (WT) mice were injected intraperitoneally with 0.3 mg/animal (~15 mg/Kg body weight) ATRA or vehicle (DMSO) daily for a period of 5 days. Type I NKT cells were purified and cultured in vitro with increasing concentrations of αGalCer. Cell proliferation was measured and supernatants were collected. The cytokine response of the isolated type 1 NKT after in vitro challenge with αGalCer was determined by sandwich ELISA for IFN-γ, IL-4, IL-6, IL-10, IL-12, and IL-13. The type I NKT cells isolated from ATRA injected mice did not proliferate in response to αGalCer stimulation (data not shown). As shown in FIG. 8c, type I NKT cells isolated from vehicle (DMSO) injected mice secrete IFN-γ, IL-4, and IL-13 in response to αGalCer stimulation, but not IL-6, IL-10, or IL-12. No secretion of IFN-γ, IL-6, IL-10, IL-12, or IL-13 in response to αGalCer stimulation was detected from type I NKT cells isolated from ATRA injected mice. Reduced levels of IL-4 secretion were observed from type I NKT cells isolated from ATRA injected mice in response to αGalCer stimulation. See FIG. 8c.

Example 10

ATRA does not Inhibit Class II MHC-Restricted Conventional CD4 T Cells

The effect of ATRA on class II MHC-restricted conventional CD4 T Cells was tested by isolating myelin basic protein MBPAc1-9-reactive CD4+ T cells from naïve B10.PL Vβ8.2 TCR transgenic mice and culturing the cells in vitro with [$^3$H]-thymidine and an optimal concentration of MBPAc1-9 in the presence or absence of graded concentrations of ATRA (0.15, 1.2, 18.8 μg/ml). Proliferation of the MBPAc1-9-reactive CD4+ T cells was measured by [$^3$H]-thymidine incorporation. No inhibition of MBPAc1-9-stimulated proliferation was observed in ATRA treated cultures. See FIG. 10. This suggests that ATRA does not directly inhibit the activity of MHC-restricted CD4+ T cells.

Example 11

Figure 11:
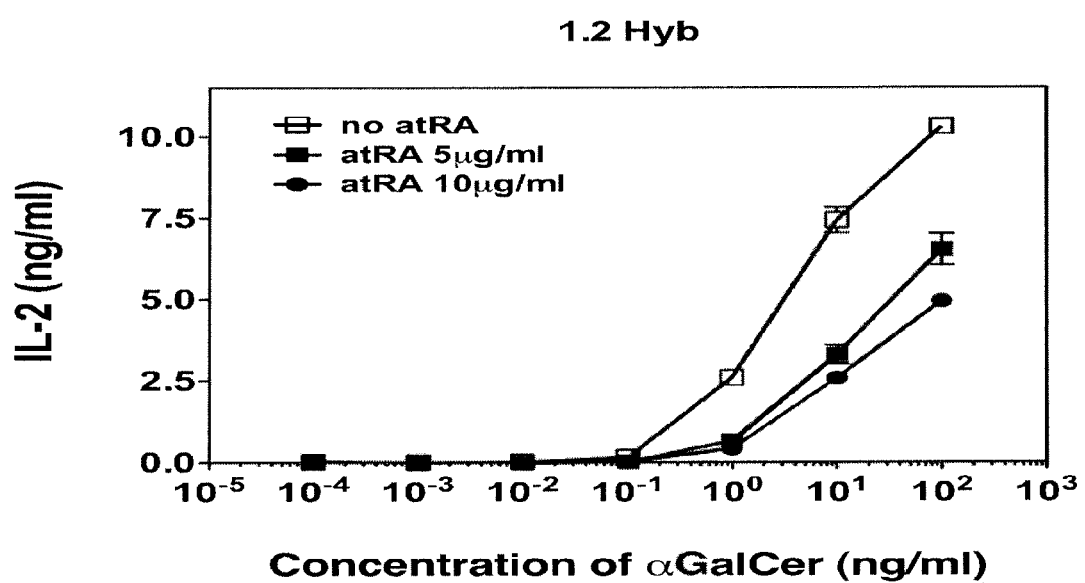
FIG. 11 shows a graph depicting the level of IL-2 secreted by Type I NKT cells (Hy1.2) cultured in vitro with graded concentrations of the lipid antigen, αGalCer, and 0, 5, or 10 μg/ml ATRA for 24 hr.
Figure 12:
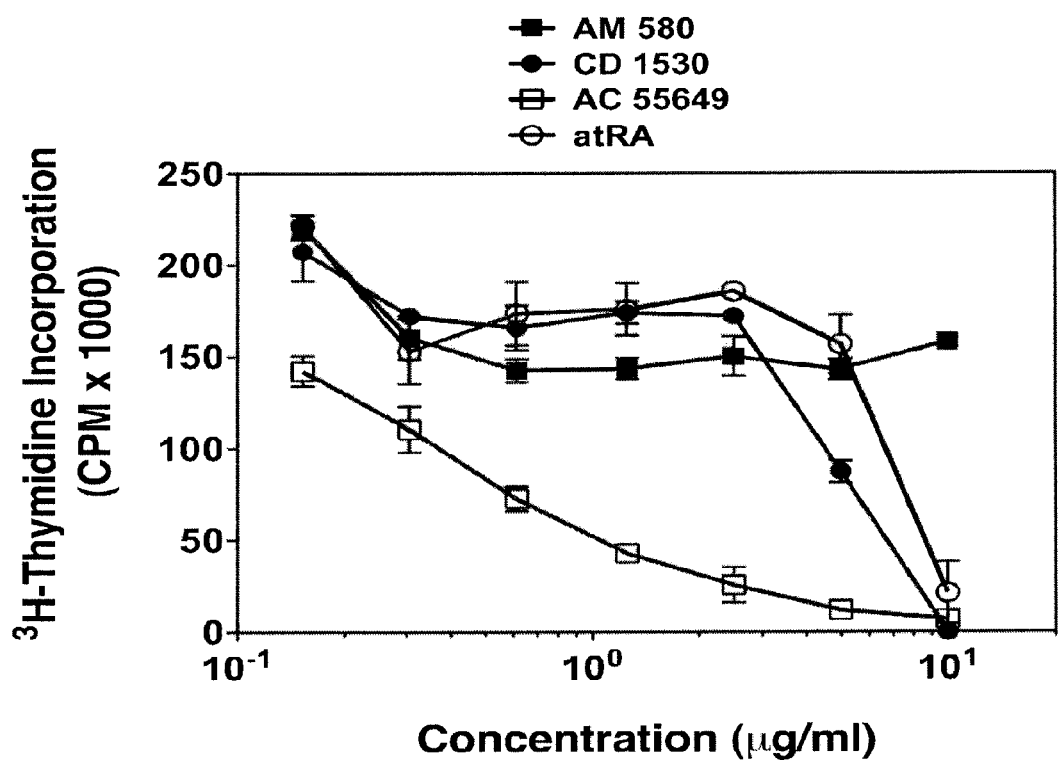
FIG. 12 shows a graph depicting proliferation (as measured by [$^3$H]-thymidine incorporation) of freshly isolated type I NKT splenic cells cultured in the presence of αGalCer and graded concentrations of ATRA, an agonist of RARα (AM580), an agonist of RAR β 2 (AC55649) or an agonist of RARγ (CD1530).

ATRA Treatment in the Absence of Antigen-Presenting Cells Inhibits Type 1 NKT Cell Function The effect of ATRA treatment on type I NKT cells in the absence of antigen-presenting cells was also measured. Type I NKT hybridoma cells (Hy1.2) were cultured in vitro either without ATRA or with 5 μg/ml, 10 μg/ml, or 20 μg/ml ATRA for 24 hr. The cells were then washed three times and co-cultured with irradiated splenocytes (APCs) in the presence of graded concentrations of the lipid antigen, αGalCer. Supernatants were collected 16 hour later and IL-2 levels were measured using IL-2 sandwich ELISA. As shown in FIG. 11, treatment of type I NKT hybridoma cells (Hy1.2) with ATRA inhibits IL-2 secretion. This suggests that ATRA treatment in the absence of antigen-presenting cells inhibits the effector function of type I NKT cells.

Example 12

Inhibition of Type I NKT Cell Activity by Subtype-Specific RAR Agonists

Retinoic acid receptors (RARs) comprise three major subtypes: RARα, RAR β, and RARγ. The RAR agonist ATRA is not selective for a specific subtype. The contribution of RAR subtypes to inhibition of type I NKT cell activity was tested with subtype-selective RAR agonists as follows. Splenic cells were isolated from naïve B6 (WT) mice and cultured in vitro in the presence of [$^3$H]-thymidine, an optimal concentration of αGalCer, and graded concentrations of the pan-RAR agonist ATRA, the RARα agonist AM580, the RAR β 2 agonist AC55649 or the RARγ agonist CD1530. Proliferation of the type I NKT cells in response to αGalCer stimulation was measured by [$^3$H]-thymidine incorporation.

Type I NKT cells cultured in the presence of ATRA, AM580, and CD1530 exhibited similar levels of cell proliferation up to a concentration of $10^1$ μg/ml. See FIG. 12. Cells cultured in the presence of $10^1$ μg/ml ATRA or CD1530 exhibited low or minimal proliferation, while proliferation was maintained for cells cultured in $10^1$ μg/ml AM580. Reduced cell proliferation compared to the other RAR agonists was observed for the RAR β 2 agonist, AC55649, at all concentrations tested, with the exception of $10^1$ μg/ml, at which concentration low or minimal proliferation was observed for cells cultured in AC55649, ATRA or CD1530.

These results suggest that the RAR β 2 agonist, AC55649 is an effective inhibitor of type I NKT cell activity and that the retinoic acid receptor-β2 (RAR-β 2) signaling pathway is involved in the inhibition of type I NKT cells.

Example 13

Effect of PPAR-γ Pathway Modulation on Type I NKT Cells

Peroxisome proliferator-activated receptors (PPARs) are ligand-inducible transcription factors that belong to the nuclear hormone receptor superfamily, which also includes the receptors for thyroid hormone, retinoids, steroid hormones and vitamin D. PPARs regulate gene expression by binding with Retinoid X Receptor (RXR) as a heterodimeric partner to specific Peroxisome Proliferator Response Elements (PPREs) in the DNA. PPARs have been implicated as playing a role in lipid and energy metabolism, inflammation, embryo implantation, diabetes and cancer.

Figure 13:
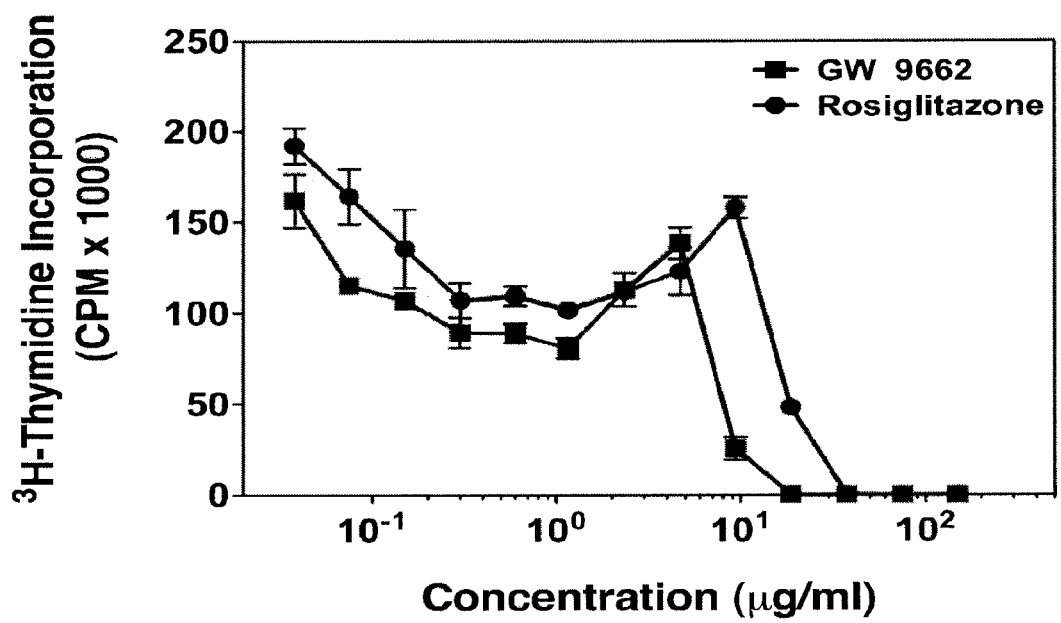
FIG. 13 shows a graph depicting proliferation (as measured by [$^3$H]-thymidine incorporation) of freshly isolated type I NKT splenic cells cultured in the presence of αGalCer and graded concentrations of an agonist of PPAR-γ (rosiglitazone) or an antagonist of PPAR-γ (GW9662).

The role of the PPAR-γ pathway in the inhibition of type I NKT cells was tested by culturing freshly isolated splenic type I NKT cells with [$^3$H]-thymidine and an optimal concentration of αGalCer in the presence or absence of graded concentrations of the PPAR-γ agonist rosiglitazone or the PPAR-γ antagonist GW9662. Proliferation of the splenic type I NKT cells in response to αGalCer stimulation was quantified by [$^3$H]-thymidine incorporation. Similar levels of proliferation was observed for cells cultured in either the PPAR-γ agonist, rosiglitazone, or the PPAR-γ antagonist, GW9662, at all concentrations. See FIG. 13. These results suggest that specific inhibition or activation of the PPAR-γ pathway does not directly inhibit type I NKT cell proliferation.

Example 14

Examination of the Effect of Retinol Analogs on Type I NKT Cell Activity

Figure 14:
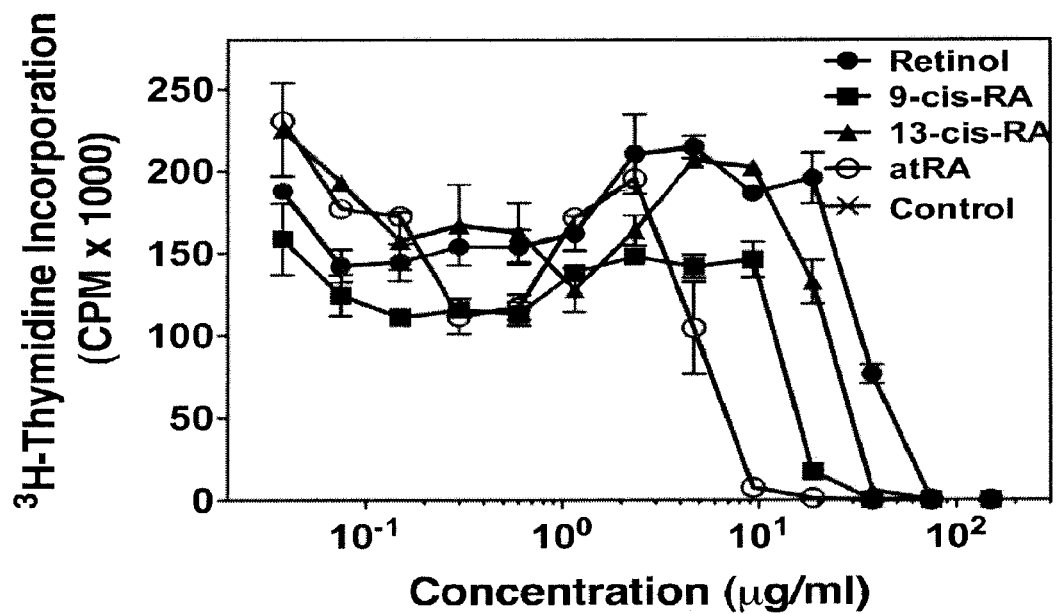
FIG. 14 shows a graph depicting proliferation (as measured by [$^3$H]-thymidine incorporation) of freshly isolated type I NKT splenic cells cultured in the presence of αGalCer and graded concentrations of ATRA, different retinoic acid analogs, Retinol or Vitamin A.

Splenic cells were isolated from naïve B6 mice and cultured in vitro with [$^3$H]-thymidine and an optimal concentration of αGalCer in the presence or absence of graded concentrations of ATRA, Retinol, 9-cis-RA or 13-cis-RA. Proliferation of the splenic type I NKT cells in response to αGalCer stimulation was quantified by [$^3$H]-thymidine incorporation. As shown in FIG. 14, no or minimal proliferation was observed for cells cultured in $10^1$ μg/ml ATRA, while the same level of inhibition of type I NKT cell proliferation was only observed at concentrations of Retinol, 9-cis-RA or 13-cis-RA which exceeded $10^1$ μg/ml.

Example 15

Examination of the Effect of RAR Agonists on Type I NKT Cell Activity

Figure 15:
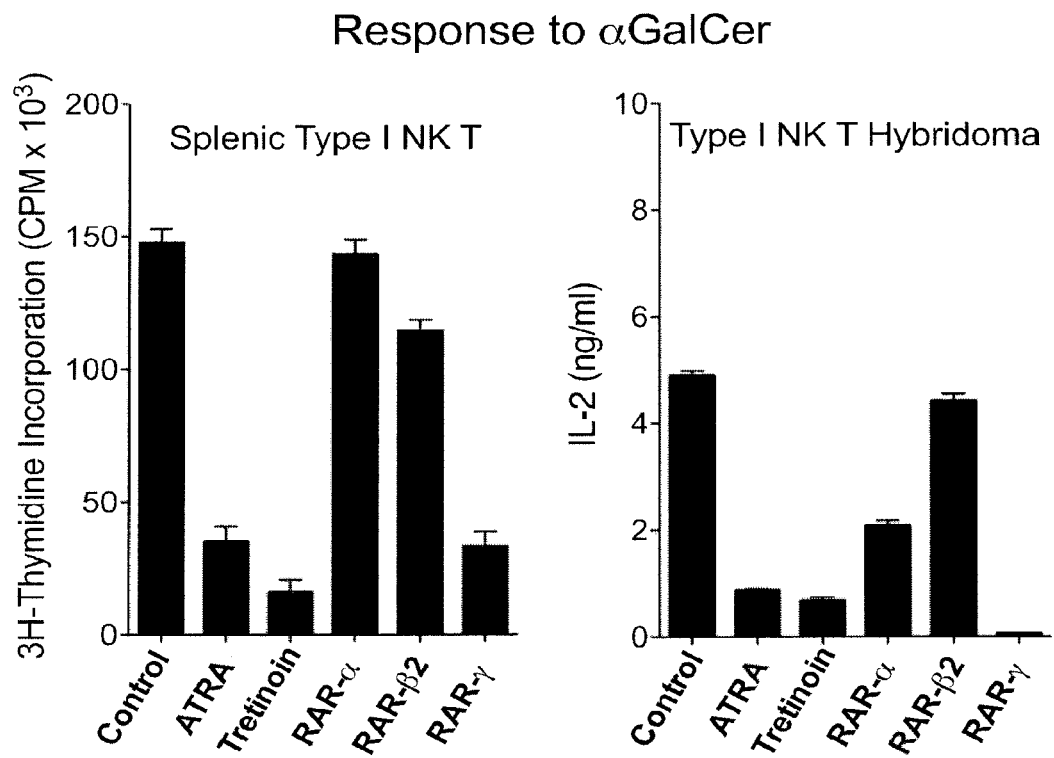
FIG. 15 shows bar graphs depicting the proliferation (as measured by [$^3$H]-thymidine incorporation) of freshly isolated type I NKT splenic cells (left) or type I NKT cell hybridoma (1.2 Hyb) cultured in the presence of optimal concentrations of αGalCer (10 ng/ml) and optimal concentrations of ATRA, Tretinoin, an agonist of RARα (AM580), an agonist of RAR β 2 (AC55649) or an agonist of RARγ (CD1530). The graphs are representative of the data of 3 independent experiments.

In vitro proliferation and cytokine release assays were performed on freshly isolated splenocytes and type I NKT cell hybridomas (1.2 Hyb). The cells were cultured in the presence of [$^3$H]-thymidine and an optimal concentration of αGalCer (10 ng/ml) with titrating concentrations of ATRA, Tretinoin, the RARα agonist AM580, the RAR β agonist AC55649 or the RARγ agonist CD1530. Proliferation of the type I NKT cells in response to αGalCer stimulation was quantified by [$^3$H]-thymidine incorporation. IL-2 levels were measured using IL-2 sandwich ELISA. Optimal concentrations of the RAR agonists was determined. A comparison of the effect of the RAR agonists at their optimum concentrations is shown in FIG. 15. The lowest levels of proliferation were observed for cells cultured in the presence of ATRA, Tretinoin, the RARγ agonist CD1530. Cells cultured in the presence of the RARγ agonist CD1530 showed the lowest levels of IL-2 secretion. These results indicate that the RARγ agonist CD1530 is an effective inhibitor of type I NKT cell activity.

Example 16

Comparison of Tazarotene and ATRA Inhibition of Type I NKT Cells

The effect of the selective RARγ agonist, Tazarotene, on type I NKT cell activity was examined by in vitro proliferation and cytokine release assays.

Figure 16:
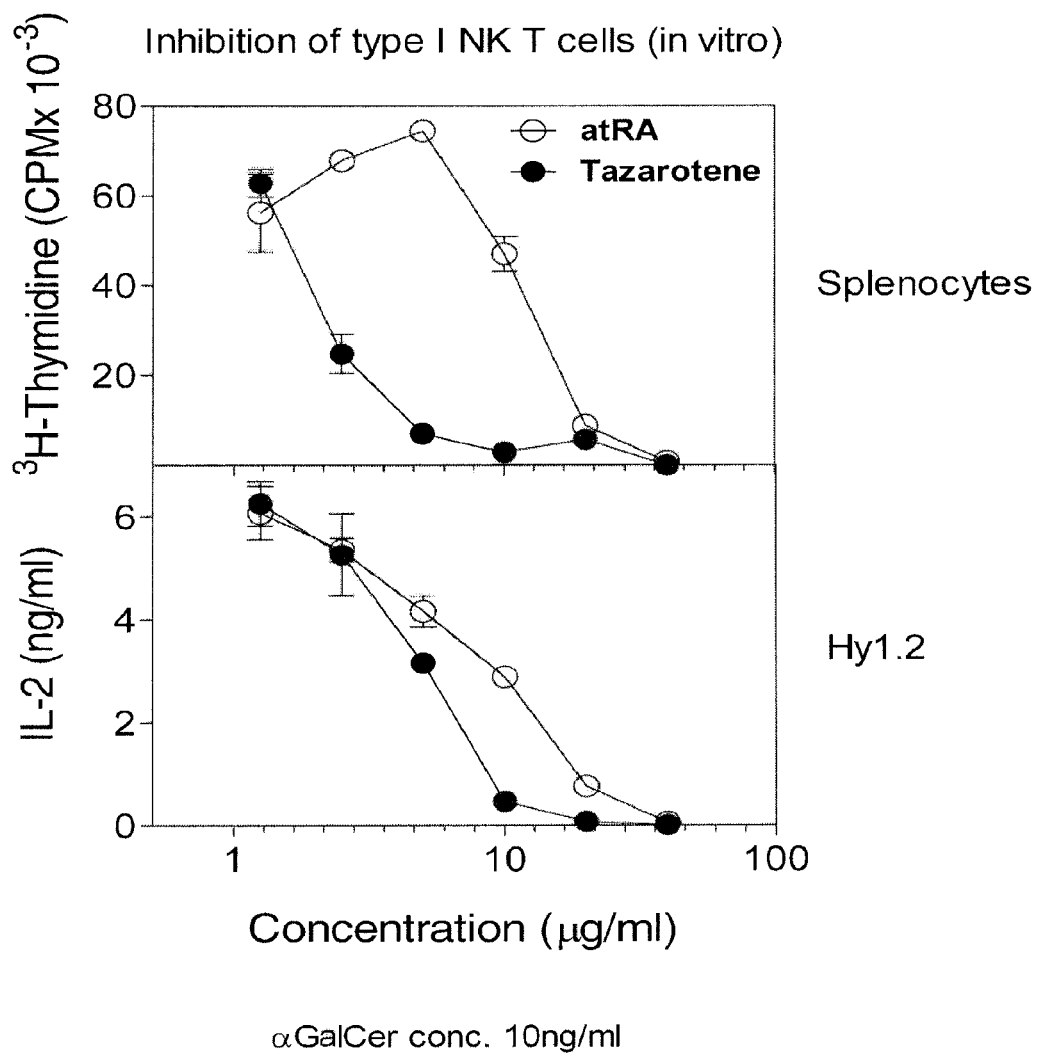
FIG. 16 shows graphs depicting the results of in vitro proliferation of freshly isolated splenocytes (top panel) or cytokine release assays of type I NKT cell hybridoma (1.2 Hyb) (bottom panel) cultured with optimal concentrations of αGalCer (10 ng/ml) in the presence of increasing concentrations of ATRA or the selective RARγ agonist Tazarotene. Tazarotene shows better inhibition of type I NKT cells than ATRA.

In vitro proliferation and cytokine release assays were performed on freshly isolated splenocytes and type I NKT cell hybridomas (1.2 Hyb). The cells were cultured in the presence of [$^3$H]-thymidine and an optimal concentration of αGalCer (10 ng/ml) with increasing concentrations of ATRA or Tazarotene. Proliferation of the type I NKT cells in response to αGalCer stimulation was quantified by [$^3$H]-thymidine incorporation. IL-2 levels were measured using IL-2 sandwich ELISA. A comparison of type I NKT cell inhibition by ATRA and Tazarotene is shown in FIG. 16. While by RAR agonists inhibit type I NKT cell proliferation and IL-2 secretion, Tazarotene achieves its inhibitory effects at lower concentrations. See FIG. 16.

Example 17

Figure 17:
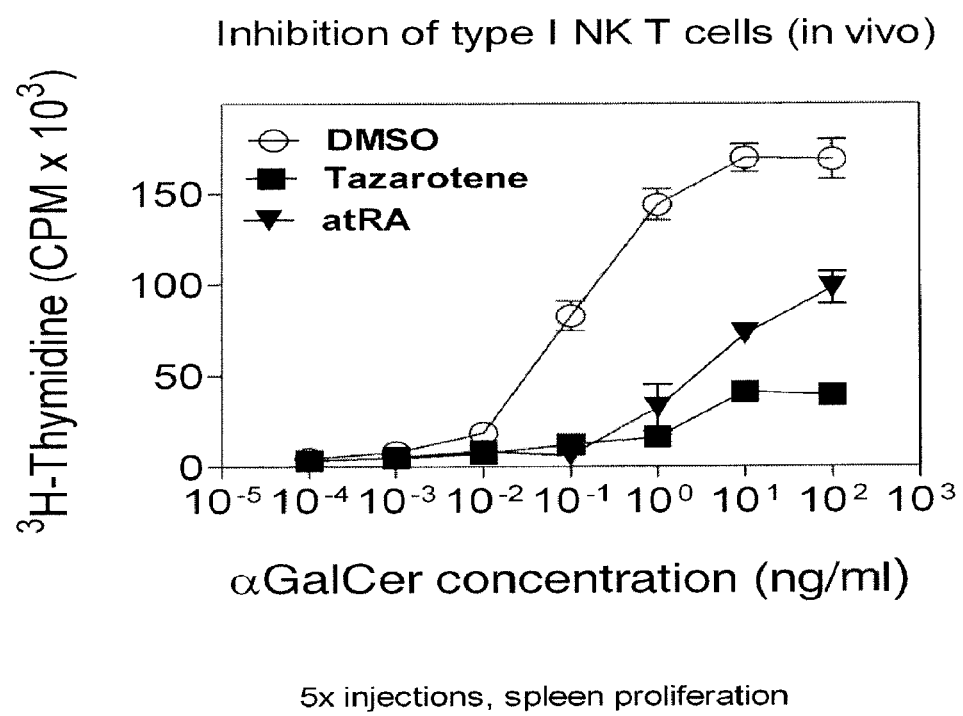
FIG. 17 shows a graph depicting the results of a ex vivo in proliferation assay of type I NKT cells isolated from mice treated with Tazarotene, ATRA or DMSO (control) and stimulated with titrated concentrations of αGalCer.

Inhibition of Type I NKT Cells Following In Vivo Administration of Tazarotene and ATRA Functional changes in type I NKT cells following in vivo administration of Tazarotene or ATRA was tested. Groups of mice were injected intraperitoneally with 300 μg ATRA (15 mg/kg), 300 μg Tazarotene (15 mg/kg) or vehicle (DMSO) daily for a period of 5 days. Splenic Type I NKT cells were purified and cultured in vitro with increasing concentrations of αGalCer. Cell proliferation was measured by quantification of [$^3$H]-thymidine incorporation and the results are shown at FIG. 17. A comparison of the proliferative response of cells isolated from ATRA injected, Tazarotene injected, or vehicle (DMSO) injected mice to αGalCer stimulation, indicates that in vivo administration of either ATRA or Tazarotene inhibits type I NKT cell activity. The lowest levels of proliferation, however, were observed for type I NKT cells isolated from Tazarotene injected mice. See FIG. 17.

Figure 18:
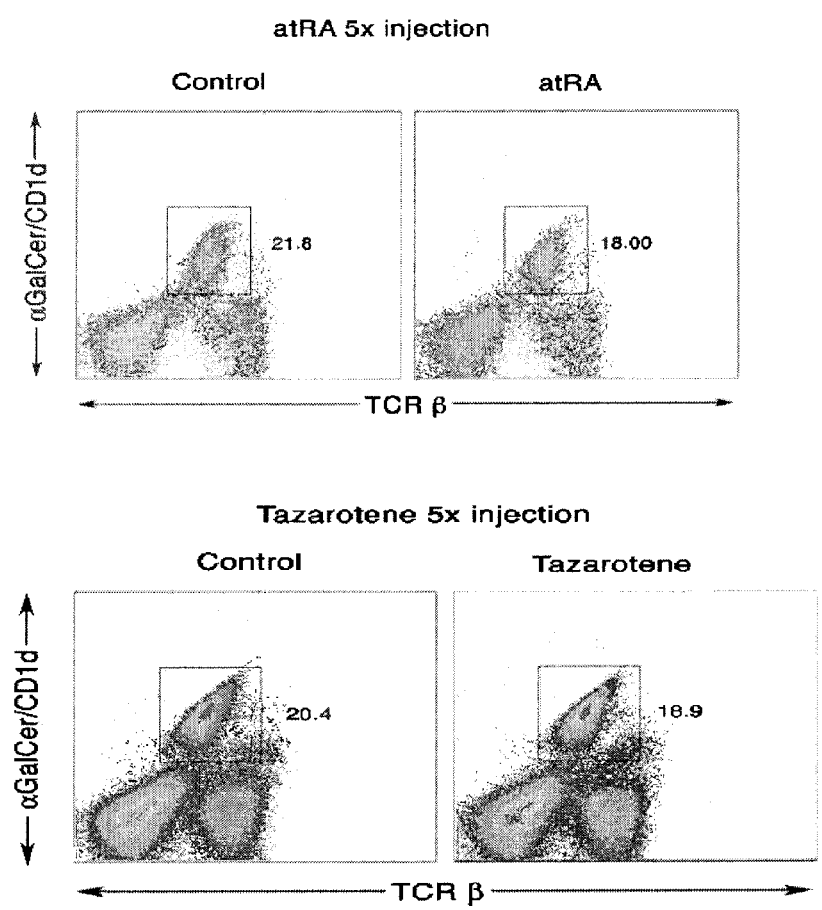
FIG. 18 shows the analysis of mononuclear cells isolated from livers of mice injected with ATRA, Tazarotene or DMSO (control) and stained with αGalCer/CD1d-tetramers and pan-anti-TCRPβ chain antibodies by flowcytometry. Type I NKT cells are indicated a box. There was no significant difference in the numbers (shown next to the box) of type I NKT cells in control vs. ATRA or Tazarotene administered animals.

Mononuclear cells were isolated from livers of mice injected with either ATRA, Tazarotene or vehicle (DMSO) and stained with αGalCer/CD1d-tetramer and a pan anti-TCR (antibodies. Flowcytometry was performed and the population of αGalCer/CD1d-tetramer/TCRPβ expressing cells (type I NKT cells) was quantified as shown in FIG. 18. No significant difference in the numbers of type I NKT cells in the livers of control vs. ATRA or Tazarotene administered animals was observed. See FIG. 18. These results indicate that ATRA or Tazarotene administration does not deplete liver type I NKT cells.

Prophetic Example 18

Prevention of ALD by RAR Agonist Administration

The effectiveness of RAR Agonists in the prevention or mitigation of alcoholic liver disease is tested by injecting groups of mice with an effective amount of: ATRA, Tazarotene, Tretinoin, the RARα agonist AM580, the RAR β agonist AC55649, the RARγ agonist CD1530, or vehicle/DMSO daily for a period of 5 days during which time the mice are either a liquid diet containing 5% ethanol for 10 days followed by (on day 11) a single high dose of gavaged ethanol (5 g/kg body weight) (chronic plus binge ethanol feeding group) or an isocaloric dextrin maltose-containing diet followed by an isocaloric gavage of with dextrin maltose (control group). The mice are euthanized 6-8 hours following gavage and serum and liver tissue is harvested.

Serum ALT levels are determined for each group of mice. Serum ALT levels are expected to be significantly increased in vehicle/DMSO injected mice subjected to chronic plus binge ethanol feeding compared to control fed mice. Chronic plus binge ethanol fed Mice receiving injections of ATRA, Tazarotene, Tretinoin, AM580, AC55649, CD1530 are expected to have reduced serum ALT levels compared to vehicle/DMSO injected mice subjected to chronic plus binge ethanol feeding. The serum ALT levels of ATRA, Tazarotene, or Tretinoin injected mice subjected to chronic plus binge ethanol feeding are expected to be similar to those observed in control fed mice. Histological examination for hepatic steatohepatitis (fatty liver disease) is expected to show significant damage of the liver tissue harvested from vehicle/DMSO injected mice following chronic plus binge ethanol feeding, while reduced or no damage is expected for liver tissue harvested from ATRA, Tazarotene, Tretinoin, AM580, AC55649, or CD1530 injected mice following chronic plus binge ethanol feeding.

Prophetic Example 19

Adoptive transfer experiments are used with αGalCer/CD1d-tetramer-purified type I NKT cells from ATRA-treated or Tazarotene-treated BL/6 mice to examine whether a graded number of these cells when transferred into naïve BL/6 recipients can inhibit liver injury following chronic plus binge ethanol feeding.

Purified (sorted) sulfatide-CD d-tetramer+ T cells are tested to determine if they can prevent ALD upon adoptive transfer into CD1d+/+ and CD1d-/- mice. Cytokine knock-out mice are used as donors of sulfatide-reactive T cells to directly determine the role of IFN-γ, IL-4 and IL-10 secretion by type II NK T cells in the regulation of ALD. Sulfatide-reactive T cells are isolated using tetramers and graded numbers (0.5-1 million) are adoptively transferred into CD1d+/+ and CD1d-/-C57BL/6 recipients. Around 1.5 million sulfatide-CD1d-tetramer+ cells are isolated from 18 naïve C57BL/6 mice. One day later recipients are exposed to chronic plus binge ethanol feeding. For analyzing the roles of cytokine secretion by type II NKT cells, initially the IFN-γ, IL-4−/− or IL-10−/− are used on the BL/6 background (Jackson Lab). Groups of BL/6 wild type, or knockout mice are injected with sulfatide (20 µg/animal) and then ALD induced. In the absence of these type 2 cytokines, sulfatide administration is expected to prevent ALD. Adoptive cell-transfer experiments are further performed with sulfatide-CD1d-tetramer+ cells from specific cytokine knockout mice, where graded numbers (0.5-1 million) are transferred into CD1d−/−C57BL/6 mice. One day later recipient mice are kept on ethanol feeding. In parallel, sulfatide-CD1d-tetramer+ T cells are transferred from wild-type mice into CD1d+/+BL/6 mice as a positive control. These experiments are expected to confirm directly the role of these cytokines secreted by sulfatide-reactive T cells in the control of ALD.

EQUIVALENTS

The foregoing written specification is considered to be sufficient to enable one skilled in the art to practice the present embodiments. The foregoing description details certain preferred embodiments and describes the best mode contemplated by the inventors. It will be appreciated, however, that no matter how detailed the foregoing may appear in text, the present embodiments may be practiced in many ways and should be construed in accordance with the appended claims and any equivalents thereof.

What is claimed:

1. A method of treating an inflammatory condition of the liver in a subject in need thereof, the method comprising administering an amount of RARγ-selective agonist sufficient to inhibit activation of pro-inflammatory type I NKT cells to the subject,
   wherein the administered RARγ-selective agonist inhibits activation of pro-inflammatory type I NKT cells in the subject, thereby treating the inflammatory condition of the liver.

2. The method of claim 1, wherein the inflammatory condition of the liver is selected from the group consisting of: fatty liver disease, alcohol induced hepatitis, non-alcoholic steatosis hepatitis, cirrhosis, fulminating cirrhosis, idiopathic hepatitis, viral-induced hepatitis (A, B, C and other), inflammatory hepatitis associated with hepato-biliary carcinoma, ischemic reperfusion injury, and solid organ transplantation.

3. The method of claim 1, wherein the inflammatory condition of the liver is an alcohol-induced liver injury selected from the group consisting of: alcohol-related liver disease, fatty liver disease, hepatic steatosis, alcoholic hepatitis and alcoholic cirrhosis.

4. The method of claim 1, wherein the inflammatory condition of the liver is alcoholic liver disease.

5. The method of claim 1, wherein the inflammatory condition of the liver is hepatic reperfusion injury.

6. The method of claim 1, wherein the inflammatory condition of the liver is hepatic steatosis.

7. The method of claim 1, wherein the amount of the RARγ-selective agonist is about 1 mg/day to about 50 mg/day.

* * * * *